(12) United States Patent
Ward et al.

(10) Patent No.: US 7,449,559 B2
(45) Date of Patent: Nov. 11, 2008

(54) TRUNCATED EGF RECEPTOR

(75) Inventors: Colin Wesley Ward, Carlton (AU); Neil Moreton McKern, North Balwyn (AU); George Oscar Lovrecz, North Balwyn (AU); Robert Nicholas Jorissen, Keysborough (AU); Thomas Peter John Garrett, Brunswick (AU); Thomas Charles Elleman, Westmeadows (AU); Antony Wilkes Burgess, Camberwell (AU); Timothy Edward Adams, Rosanna (AU); Teresa Anne Domagala, Alexandria (AU); Edouard Collins Nice, St. Kilda (AU)

(73) Assignees: Commonwealth Scientific and Industrial Research Organisation, Campbell (AU); Ludwig Insitutute for Cancer Research, Zurich (CH)

(*) Notice: Subject to any disclaimer, the term of this patent is extended or adjusted under 35 U.S.C. 154(b) by 210 days.

(21) Appl. No.: 11/209,187

(22) Filed: Aug. 22, 2005

(65) Prior Publication Data
US 2006/0234343 A1 Oct. 19, 2006

Related U.S. Application Data

(63) Continuation-in-part of application No. 10/070,007, filed as application No. PCT/AU01/00782 on Jun. 28, 2001, now Pat. No. 6,946,543.

(30) Foreign Application Priority Data

Jun. 28, 2000 (AU) .................................... PQ 8418

(51) Int. Cl.
| | | |
|---|---|---|
| *A61K 38/17* | (2006.01) | |
| *C07K 14/71* | (2006.01) | |
| *C07K 16/46* | (2006.01) | |

(52) U.S. Cl. ................... 530/402; 530/350; 530/387.1; 514/12

(58) Field of Classification Search ....................... None
See application file for complete search history.

(56) References Cited

U.S. PATENT DOCUMENTS

| | | |
|---|---|---|
| 5,218,090 A | 6/1993 | Conners |
| 5,708,156 A | 1/1998 | Ilekis |
| 6,696,290 B2 | 2/2004 | Fitspatrick et al. |
| 2002/0002276 A1 | 1/2002 | Fitzpatrick et al. |
| 2003/0190702 A1 | 10/2003 | Maile et al. |

FOREIGN PATENT DOCUMENTS

| | | | |
|---|---|---|---|
| WO | WO 91/03489 | | 3/1991 |
| WO | WO 9919488 A1 | * | 4/1999 |
| WO | WO 99/62955 | | 12/1999 |

OTHER PUBLICATIONS

Zhou et al., ErbB-4: a receptor tyrosine kinase, Inflamm. Res. 51:091-101, 2002.*

Junttila et al., ErbB4 and its isoforms: Selective regulation of growth factor responses by naturally occurring receptor variants, TCM 10(7): 304-310, 2000.*

Jorissen te al., Characterization of a comparative model of the extracellular domain of the epidermal growth factor receptor, Protein Sci., 9: 310-324, 2000.*

Riese te al., The epidermal growth factor receptor couples transforming growth factor-alpha, heparin-binding epidermal growth factor-like factor, and amphiregulin to neu, ErbB-3, and ErbB-4, J. Biol. Chem. 271(16): 20047-20052, Aug. 16, 1996.*

Ashkenazi et al. (1997) "Immunoadhesins as Research Tools and Therapeutic Agents," *Curr. Opin. Immunol.* 9:195-200.

Bajaj et al. (1987) "On the Tertiary Structure of the Extracellular Domains of the Epidermal Growth Factor and Insulin Receptors," *Biochim. Biophys. Acta.* 916:220-226.

Bishayee et al. (2000) "Role of Conformational Alteration in The Epidermal Growth Factor Receptor (EFGFR) Function," *Biochem. Pharmacol.* 60:1217-1223.

Burgess et al. (1994) "Growth Factors and Their Receptors: New Opportunities for Cancer Treatment," *Pathology* 26:453-463.

Carter, P. (1987) "Improved Oligonucleotide-Directed Mutagenesis Using M13 Vectors," *Methods Enzymol* 154:382-403.

Catimel et al. (1999) "Recent Applications of Instrumental Biosensors for Protein and Peptide Structure-Function Studies," *Protein Pep. Lett.* 6:319-340.

Catimel et al. (1997) "Kinetic Analysis of the Interaction Between the Monoclonal Antibody A33 and its Colonic Epithelial Antigen by the Use of an Optical Biosensor," *J. Chromatogr.* 776:15-30.

De Crescenzo et al. (2000) "Real-Time Kinetic Studies on the Interaction of Transforming Growth Factor α With the Epidermal Growth Factor Receptor Extracellular Domain Reveal a Conformational Change Model," *Biochem.* 39:9466-9476.

(Continued)

*Primary Examiner*—Lorraine Spector
*Assistant Examiner*—Claire Kaufman
(74) *Attorney, Agent, or Firm*—Greenlee, Winner and Sullivan, P.C.

(57) ABSTRACT

The present invention relates to truncated EGF receptor molecules that exhibit increased binding affinities for EGFR ligands such as EGF and TGF1. The present invention also relates to methods of screening for EGF receptor ligands and methods of treatment which involve the use of these molecules.

13 Claims, 11 Drawing Sheets

OTHER PUBLICATIONS

Domagala et al. (2000) "Stoichiometry, Kinetic and Binding Analysis of the Interaction Between Epidermal Growth Factor (EGF) and the Extracellular Domain of the EGF Receptor," *Growth Factors* 18:11-29.

Ekstrand et al. (1992) "Amplified and Rearranged Epidermal Growth Factor Receptor Genes in Human Gliblastomas Reveal Deletions or Sequences Encoding Portions of the N- and/or C-Terminal Tails," *Proc. Natl. Acad. Sci. USA* 89:4309-4313.

Elleman et al. (2001) "Identification of a Determinant of Epidermal Growth Factor Receptor Ligand-Binding Specificity Using a Truncated, High-Affinity Form of the Ectodomain," *Biochem.* 40(30):8930-8939.

Fitzpatrick et al. (1999) "Formation of High Affinity Heregulin Binding Site Using the Soluble Extracellular Domains of ErbB2 with ErbB3 or ErbB4," *FEBS Lett.* 431:102-106.

Garrett et al. (2002) "Crystal Structure of a Truncated Epidermal Growth Factor Receptor Extracellular Domain Bound to Transforming Growth Factor," *Cell* 110(6):763-773.

Gill et al. (1984) "Monoclonal Anti-Epidermal Growth Factor Receptor Antibodies Which are Inhibitors of Epidermal Growth Factor Binding and Antagonists of Epidermal Growth Factor Binding and Antagonists of Epidermal Growth Factor-Stimulated Tyrosine Protein Kinase Activity," *J. Biol. Chem.* 259:7755-7760.

Hammacher et al. (1996) "The Interluken-6 (IL-6) Partial Antagonist (Q159E,T162P)IL-6 Interacts with the IL-6 Receptor and gp130 but Fails to Induce a Stable Hexameric Receptor Complex," 271:5464-5473.

Hynes, N.E. (1993) "Amplification and Overexpression of the *erbB*-2 Gene in Human Tumors: Its Involvement in Tumor Development, Significance as a Prognostic Factor, and Potential as a Target for Cancer Therapy," *Sem. Cancer Biol.* 4:19-26.

Jones et al. (1999) "Binding Specificities and Affinities of *efg* Domains for ErbB Receptors," *FEBS Lett.* 447:227-231.

Kohda et al. (1993) "A 40kDa Epidermal Growth Factor/Transforming Growth Factor α-Binding Domain Produced by Limited Proteolysis of the Extracellular Domain of the Epidermal Growth Factor receptor," *J. Biol. Chem.* 268:1976-1981.

Lax et al. (1988) "Chicken Epidermal Growth Factor (EGF) Receptor: cDNA Cloning, Expression in Mouse Cells, and Differential Binding of EGF and Transforming Growth Factor Alpha," *Mol. Cell. Biol.* 8:1970-1978.

Maihle et al. (1991) "Native Avian c-erbB Gene Expresses a Secreted Protein Product Corresponding to the Ligand-Binding Domain of the Receptor," *Proc. Natl. Acad. Sci. USA* 88:1825-1829.

McKern et al. (1997) "Crystallization of the First Three Domains of the Human Insulin-Like Growth Factor-1 Receptor," *Protein Sci.* 6:2663-2666.

Minton, A.P. (1994) *Modern Analytical Ultracentirfugation: Acquisition and Interpretation of Data for Biological and Synthetic Polymer Systems*, Schuster et al. eds., Birkhauser, Boston, p. 81.

Morton et al. (1998) "Kinetic Analysis of Macromolecular Interactions Using Surface Plasmon Resonance Biosensors," *Methods Enzymol* 295:268-294.

Nice et al. (1999) "Instrumental Biosensors: New Perspectives for the Analysis of Biomolecular Interactions," *BioEssays* 21:339-352.

Nice et al. (1994) "Synergies Between Micropreparative High-Performance Liquid Chromatography and an Instrumental Optical Biosensor," *J. Chromatogr. A* 660:169-185.

Norrander et al. (1983) "Construction of Improved M13 Vectors Using Oligodeoxynucleotide-Directed Mutagenesis," *Gene* 26:101-106.

Prewett et al. (1998) "Mouse-Human Chimeric Anti-Epidermal Growth Factor Receptor Antibody C225 Inhibits the Growth of Humna Renal Cell Carcinoma Xenografts n Nude Mice," *Clin. Cancer Res.* 4:2957-2966.

Reiter et al. (1996) "A 1.8kb Alternative Transcript from the Human Epidermal Growth Factor Receptor Gene Encodes a Truncated Form of the Receptor," *Nuc. Acids Res.* 24:4050-4056.

Reiter et al. (2001) "Comparative Genomic Sequence Analysis and Isolation of Human and Mouse Alternative EGFR Transcripts Encoding Truncated Receptor Isoforms," *Genomic* 71:1-20.

Rockwell (1997) "Cell-Surface Perturbations of the Epidermal Growth Factor and Vascular Endothelial Growth Factor Receptors by Phosphorothioate Oligodeoxynucleotides," *Proc. Natl. Acad. Sci. USA* 94:6523-6528.

Sandgreen et al. (1990) "Overexpression of TGFα in Transgenic Mice: Induction of Epithelial Hyperplasia, Pancreatic Metaplasia, and Carcinoma of the Breast," *Cell* 61:1121-1135.

Sanger et al. (1977) "DNA Sequencing With Chain-Terminating Inhibitors," *Proc. Natl. Acad. Sci.* 74:5463-5467.

Saxon et al. (1999) "Mutagenesis Reveals a Role for Epidermal Growth Factor Receptor Extracellular Subdomain IV in Ligand Binding," *J. Biol. Chem.* 274:28356-28362.

Souriau et al. (1997) "A Simple Luciferase Assay for Signal Transduction Activity Detection of Epidermal Growth Factor Displayed on Phage," *Nuc. Acids Res.* 25:1585-1590.

Stanley, P. (1989) "Chinese Hamster Ovary Cell Mutants with Multiple Glycosylation Defects for Production of Glycoproteins with Minimal Carbohydrate Heterogeneity," *Mol. Cell. Biol.* 9:377-383.

Ullrich et al. (1984) "Human Epidermal Growth Factor Receptor cDNA Sequence and Aberrant Expression of the Amplified Gene in A431 Epidermoid Carcinoma Cells," *Nature* 309:418-425.

Voldborg et al. (1997) "Epidermal Growth Factor Receptor (EGFR) and EGFR Mutations, Function and Possible Role in Clinical Trials," *Annals of Oncology* 8:1197-1206.

Ward et al. (1995) "Insulin and Epidermal Growth Factor Receptors Contain the Cysteine Repeat Motif Found in the Tumor Necrosis Factor Receptor," *Prot. Struct. Func. Genet.* 22:141-153.

\* cited by examiner

TRUNCATED EGF RECEPTOR

CROSS REFERENCE TO RELATED APPLICATIONS

This application is a continuation-in-part of application Ser. No. 10/070,007, filed on Oct. 10, 2002, now U.S. Pat. No 6,946,543, which is the National Phase of PCT/AU01/00782, filed Jun. 28, 2001, designating the U.S. and published as WO 02/00876, with a claim of priority from Australian application no. PQ 8418, filed Jun. 28, 2000.

All of the foregoing applications, as well as all documents cited in the foregoing applications ("application documents") and all documents cited or referenced in the application documents are incorporated herein by reference. Also, all documents cited in this application ("herein cited documents") and all documents cited or referenced in herein cited documents are incorporated herein by reference. In addition, any manufacturer's instructions or catalogues for any products cited or mentioned in each of the application documents or herein cited documents are incorporated by reference. Documents incorporated by reference into this text or any teachings therein can be used in the practice of this invention. Documents incorporated by reference into this text are not admitted to be prior art.

BACKGROUND OF THE INVENTION

The present invention relates to truncated EGF receptor molecules and to pharmaceutical compositions comprising these molecules. The present invention also relates to methods of screening for EGF receptor ligands and methods of treatment which involve the use of these molecules.

The epidermal growth factor receptor (EGFR) family consists of four distinct tyrosine kinase receptors, EGFR/HER/ErbB1, HER2/Neu/ErbB2, HER3/ErbB3 and HER4/ErbB4 (1). These receptors are widely expressed in epithelial, mesenchymal and neuronal tissues and play fundamental roles during development and differentiation. They are activated by a family of at least twelve ligands that induce either homo- or hetero-dimerisation of the EGFR homologues. ErbB2 is unable to bind ligand on its own but is a potent co-receptor for all ligands when co-expressed with other members of the EGFR/HER/ErbB family.

The EGFR is a large (1,186 residues), monomeric glycoprotein with a single transmembrane region and a cytoplasmic tyrosine kinase domain flanked by noncatalytic regulatory regions. Sequence analyses have shown that the ectodomain (residues 1-621) contains four sub-domains, here termed L1, CR1, L2 and CR2, where L and CR are acronyms for large and Cys-rich respectively (2, 3). The L1 and L2 domains have also been referred to as domains I and III, respectively (4). The CR domains have been previously referred to as domains II and IV (4), or as S1.1-S1.3 and S2.1-S2.3 where S is an abbreviation for small (2).

Many cancer cells express constitutively active EGFR (5) or other EGFR family members (6). Elevated levels of activated EGFR occur in bladder, breast, lung and brain tumours. Antibodies to EGFR can inhibit ligand activation of EGFR and the growth of many epithelial cell lines. Patients receiving repeated doses of a humanised chimeric anti-EGFR monoclonal antibody (Mab) showed signs of disease stabilization. The large doses required and the cost of production of humanised Mab is likely to limit the application of this type of therapy. These findings indicate that the development of EGF receptor antagonists may be attractive anticancer agents.

SUMMARY OF THE INVENTION

The present inventors have now made the surprising finding that the deletion of residues in the CR2 domain of the EGFR ectodomain gives rise to a truncated ectodomain with enhanced affinity for epidermal growth factors such as (EGF) and/or transforming growth factor-I (TGF-α). This finding goes against recently reported results (8) showing that deletions or mutations in the CR2 region reduce EGFR binding affinity for EGF.

As will be appreciated by those skilled in the art, the truncated EGFR ectodomains of the present invention may provide increased sensitivity in assays which screen for ligands of the EGF receptor. Furthermore, the truncated EGFR ectodomains of the present invention may have therapeutic potential given their high affinity for ligand and their ability to competitively inhibit EGF-induced proliferation responses in vitro.

Accordingly, the present invention provides a truncated EGFR ectodomain, the truncated EGFR ectodomain lacking a substantial portion of the CR2 domain such that the truncated EGFR ectodomain has an increased binding affinity for at least one EGFR ligand when compared to the full length EGFR ectodomain.

In one embodiment the present invention provides a truncated epidermal growth factor receptor (EGFR) ectodomain comprising at least residues 1-492 of ErbB1 or equivalent residues of another member of the EGFR family, the truncated EGFR ectodomain lacking at least the third to seventh modules of the CR2 domain such that the truncated EGFR ectodomain has an increased binding affinity for at least one EGFR ligand when compared to the full length EGFR ectodomain.

The EGFR ligand may be, for example, amphiregulin, heparin binding EGF, β-cellulin, EGF or TGF-α. In a preferred embodiment of the first aspect the truncated EGFR ectodomain has an increased binding affinity for EGF and/or TGF-α.

In a further preferred embodiment the truncated EGFR ectodomain lacks at least the third to seventh modules of the CR2 domain. In a further preferred embodiment, the truncated EGFR ectodomain lacks at least the second to seventh modules of the CR2 domain. The truncated EGFR ectodomain may further lack a portion of the first module of the CR2 domain.

In a further preferred embodiment the truncated EGFR ectodomain comprises at least residues 1 to 492 of ErbB1. Preferably, the truncated EGFR ectodomain lacks residues 514-621 of ErbB1. More preferably, the truncated EGFR ectodomain lacks residues 502-621 of ErbB1.

In a further preferred embodiment the member of the EGFR family is ErbB3 and the truncated EGFR comprises at least residues 1 to 491 of ErbB3. Preferably, the truncated EGFR ectodomain lacks residues 513-624 of ErbB3. More preferably, the truncated EGFR ectodomain lacks residues 501-624 of ErbB3.

In a further preferred embodiment the member of the EGFR family is ErbB4 and the truncated EGFR comprises at least residues 1 to 488 of ErbB4. Preferably, the truncated EGFR ectodomain lacks residues 510-626 of ErbB4. More preferably, the truncated EGFR ectodomain lacks residues 498-626 of ErbB4.

In a further preferred embodiment the truncated EGFR ectodomain comprises residues 1-501 or residues 1-513 of ErbB1.

In a further preferred embodiment the truncated EGFR ectodomain consists essentially of residues 1-501 or residues 1-513 of ErbB1.

In a further preferred embodiment the truncated EGFR ectodomain consists of residues 1-501 or residues 1-513 of ErbB1.

In a further preferred embodiment the member of the EGFR family is ErbB3 and the truncated EGFR ectodomain comprises residues 1-500 or residues 1-512 of ErbB3.

In a further preferred embodiment the member of the EGFR family is ErbB3 and the truncated EGFR ectodomain consists essentially of residues 1-500 or residues 1-512 of ErbB3.

In a further preferred embodiment the member of the EGFR family is ErbB3 and the truncated EGFR ectodomain consists of residues 1-500 or residues 1-512 of ErbB3.

In a further preferred embodiment the member of the EGFR family is ErbB4 and the truncated EGFR ectodomain comprises residues 1-497 or residues 1-509 of ErbB4.

In a further preferred embodiment the member of the EGFR family is ErbB4 and the truncated EGFR ectodomain consists essentially of residues 1-497 or residues 1-509 of ErbB4.

In a further preferred embodiment the member of the EGFR family is ErbB4 and the truncated EGFR ectodomain consists of residues 1-497 or residues 1-509 of ErbB4.

Further deletions or mutations may be made to the L1, CR1 and/or L2 subdomains of the truncated EGFR ectodomain of the present invention, provided that these further deletions or mutations do not substantially affect the binding affinity of the truncated EGFR ectodomain. Preferably, however, the truncated EGFR ectodomain of the present invention comprises the L1, CR1 and L2 subdomains and the first module of the CR2 subdomain.

In a further preferred embodiment, the truncated EGFR ectodomain has an affinity for EGF such that the $K_d$ is less than 30 nM, more preferably less than 25 nM.

In a further preferred embodiment, the truncated EGFR ectodomain has an affinity for TGF-α such that the $K_d$ is less than 45 nM, more preferably less than 40 nM.

The present invention also provides a polynucleotide encoding a truncated EGFR ectodomain of the present invention.

The present invention also provides an expression vector comprising a polynucleotide of the present invention.

The present invention also provides a host cell comprising an expression vector of the present invention.

The present invention also provides a method for producing a truncated EGFR ectodomain of the present invention, the method comprising culturing a host cell of the present invention under conditions which allow production of the truncated EGFR ectodomain and isolating the truncated EGFR ectodomain.

The present invention also provides a pharmaceutical composition comprising a truncated EGFR ectodomain according to the present invention and a pharmaceutically acceptable carrier or diluent.

The present invention also provides a method of screening a putative compound for the ability to modulate the activity of the EGF receptor, the method comprising exposing the putative compound to a truncated EGFR ectodomain according to the present invention and monitoring the activity of the truncated EGFR ectodomain.

A suitable assay procedure may involve a competition binding assay in a microplate format, where the putative compound is tested for its ability to inhibit the binding of labelled ligand such as EGF or TGFα to the truncated EGF receptor ectodomain. The label may be a radiolabelled tag such as $^{125}I$ or a fluorescent tag such as fluorescein isothiocyanate or a lanthanide ion such as europium.

The present invention also provides a method of treating or preventing a disease associated with signaling by a molecule of the EGF receptor family in a subject, the method comprising administering to the subject a truncated EGFR ectodomain of the present invention.

Preferably, the disease associated with signaling by a molecule of the EGF receptor family is selected from psoriasis and tumour states comprising but not restricted to cancer of the breast, brain, ovary, cervix, pancreas, lung, head and neck, and melanoma, rhabdomyosarcoma, mesothelioma and glioblastoma.

The method of treatment of the present invention may be used alone or in combination with other therapeutic measures. For example, the method may be used in combination with cytotoxic modalities, such as anti-EGFR antibodies, radiotherapy or chemotherapy, in the treatment of tumour states.

BRIEF DESCRIPTION OF THE FIGURES

FIGS. 1A and 1B: Sequence alignment of the ectodomains of human EGF receptor family proteins ErbB1, ErbB2, ErbB3 and ErbB4.

(7) (0.5 µg/ml) and horseradish-peroxidase-labelled goat anti-mouse IgG (Bio-Rad) with detection by ECL (Amersham Pharmacia Biotech). Analysis by non-reducing SDS-PAGE was necessary since the antibody used to detect ErbB1501 (Mab528) is conformation-dependent.

Figure 6:
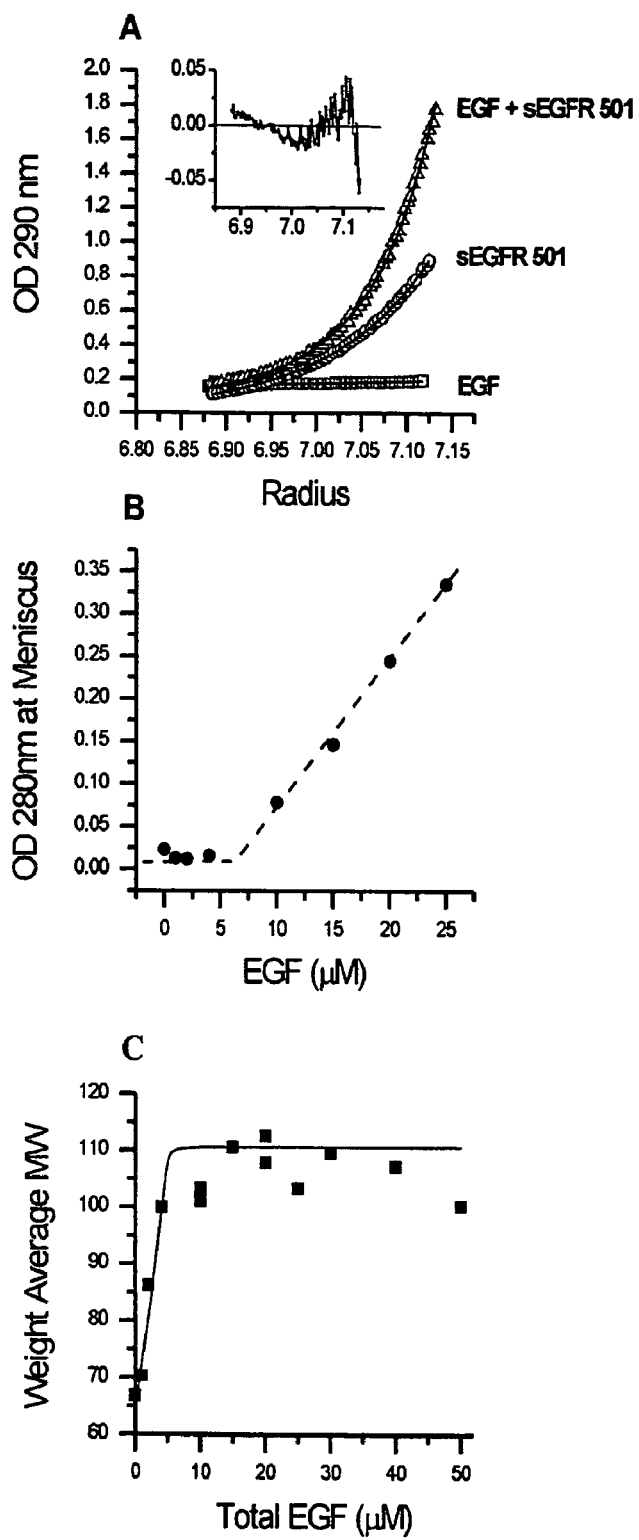

FIG. 6. Analysis of EGF/ErbB1501 (sEGFR501) interactions using the analytical ultracentrifuge. (A) Sedimentation equilibrium analysis of EGF, ErbB1501 (sEGFR501) and a mixture of EGF and ErbB1-501 (sEGFR501). The equilibrium distributions were obtained after centrifugation at 12,000 rpm at 20° C. for 16 h. (□) 20 µM EGF; (○) 10 µM ErbB1501 (sEGFR501), (Δ) 20 µM EGF+10 µM ErbB1501 (sEGFR501). The lines of best fit drawn though the data for EGF and sEGFR501 are for single species and for molecular weight values of 6,000 and 65,600 respectively. The line drawn through the data for the EGF/ErbB1501 (sEGFR501) mixture is the line of best-fit calculated assuming two species with the molecular weight of the first species fixed at 6,000 and a fitted value of 106,400 for the molecular weight of the second species. Inset: The residual plot for the fit of the EGF/ErbB1501 (sEGFR501) mixture. (B) Meniscus depletion sedimentation analysis of the stoichiometry of EGF binding to ErbB1-501 (sEGFR501). Solutions containing 5 µM ErbB1-501 (sEGFR501) and different molar ratios of EGF:EGFR were spun for 16 h at 20,000 rpm and 20° C. in the XLA analytical ultracentrifuge. Under these conditions ErbB1501 (sEGFR501) and its complexes with EGF are depleted from the meniscus leaving unbound EGF in the supernatant. Optical density measurements at 280 nm enable the amount of unbound EGF near the meniscus to be estimated. (C) Data obtained for the weight-average molecular weight of the "second" species calculated for mixtures of ErbB1501 (sEGFR501) (5 µM) and EGF at the concentrations indicated under the conditions of panel A above. The solid line corresponds to a simulated curve based on a KD of 30 nM and a dimerisation constant of 4 µM.

Figure 7:
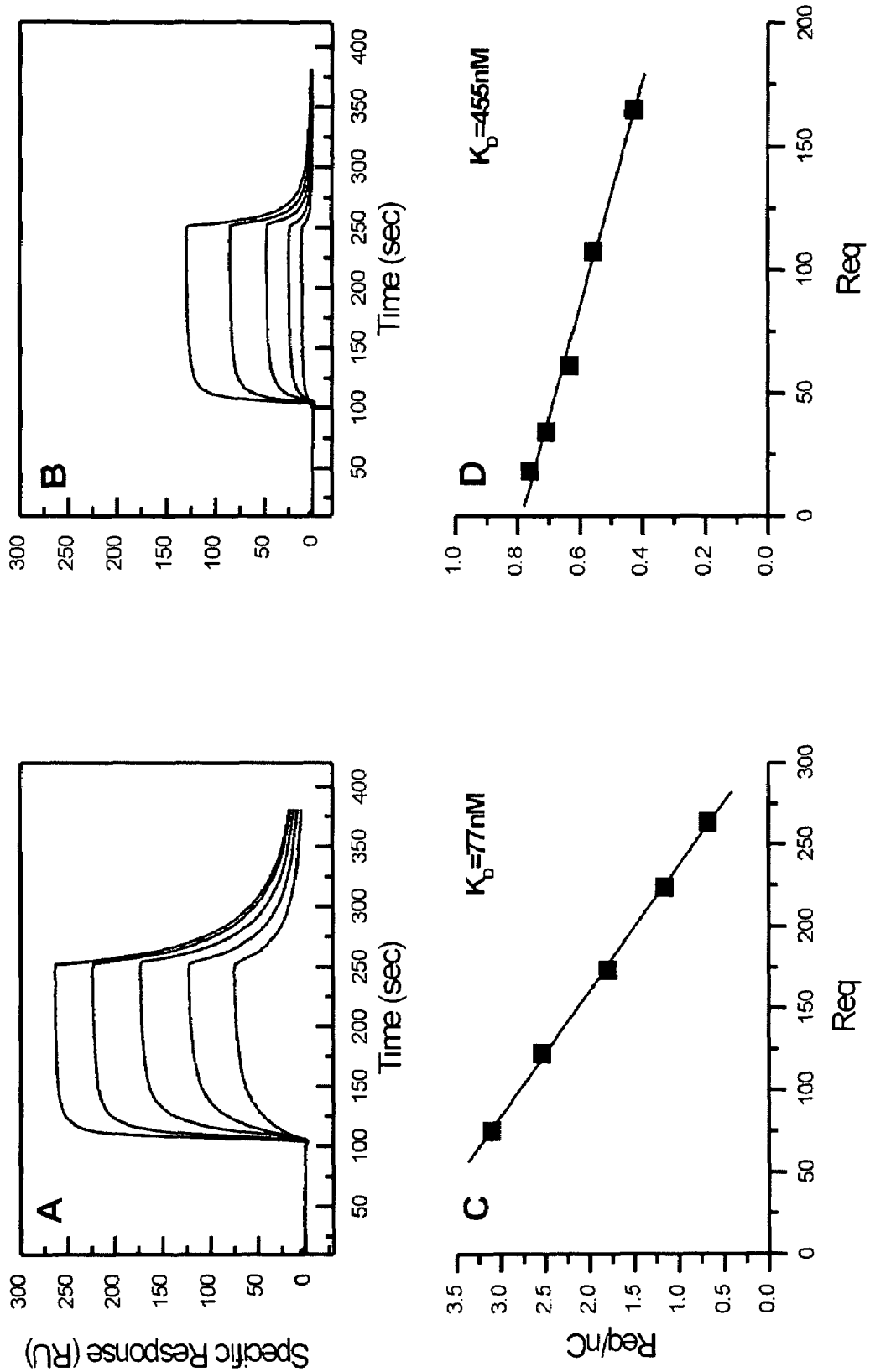

FIG. 7: BIAcore analysis of the binding of the Gly441Lys ErbB1501 mutant to immobilised hEGF and hTGF-α. Purified Gly441LyssErbB1501 (24-385 nM) was passed over immobilised hTGF-α (Panel A) or hEGF (Panel B) using the experimental conditions described in FIG. 2. The corresponding Scatchard analysis, using the equilibrium binding values obtained from these sensorgrams, is shown below (Panels C,D).

Figure 8:
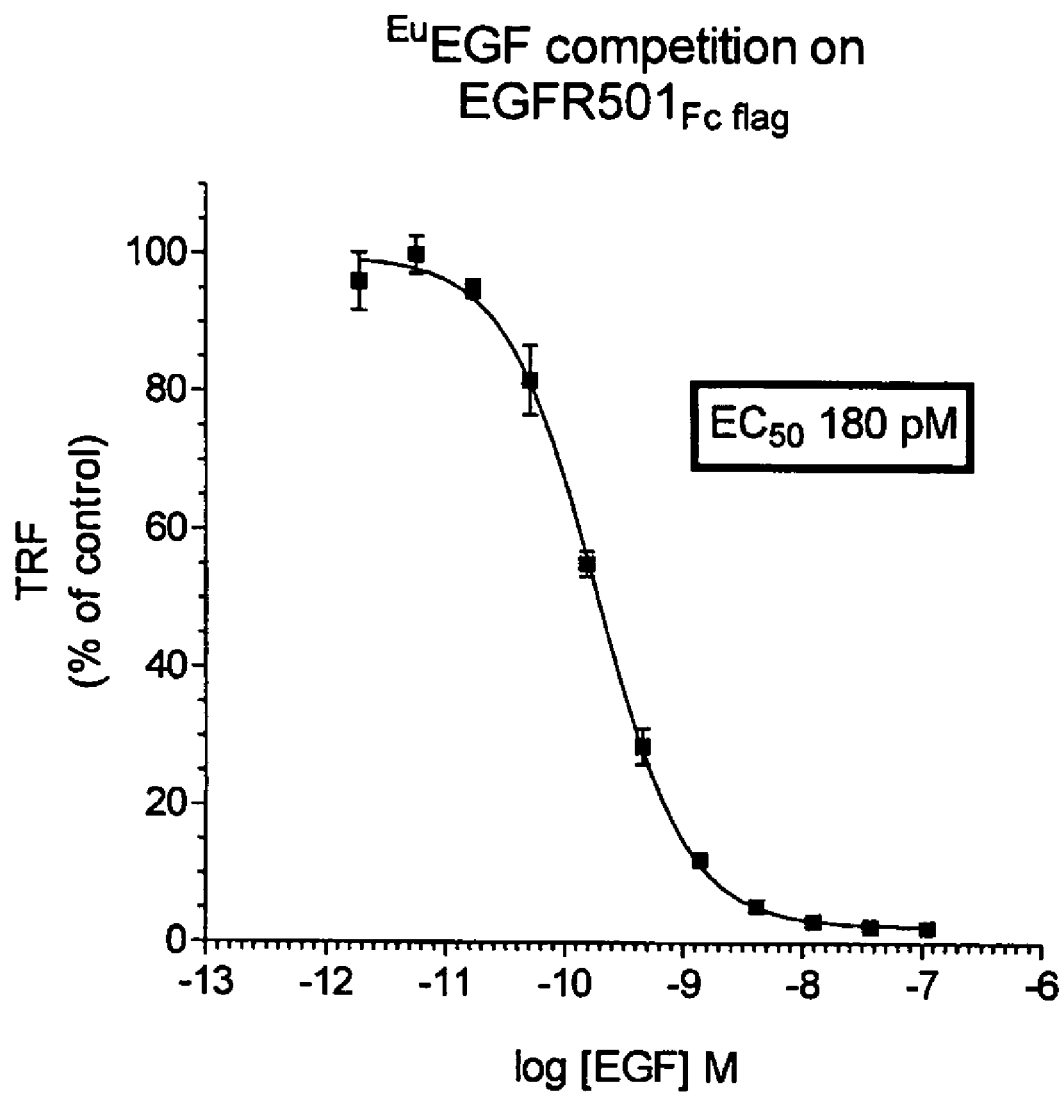

FIG. 8 $^{EU}$EGF displacement from immobilized EGFR501$_{Fcflag}$. Recombinant EGFR501Fc flag protein was immobilized by incubation in wells of a 96-well Lumitrac plate (Nunc) that had been pre-coated with protein G. Competition binding studies were performed with Europium-labelled EGF (Wallac) as trace and increasing concentrations of unlabelled EGF. After incubation overnight at 4° C., the wells were washed and the bound trace measured by time-resolved fluorescence.

Figure 9:
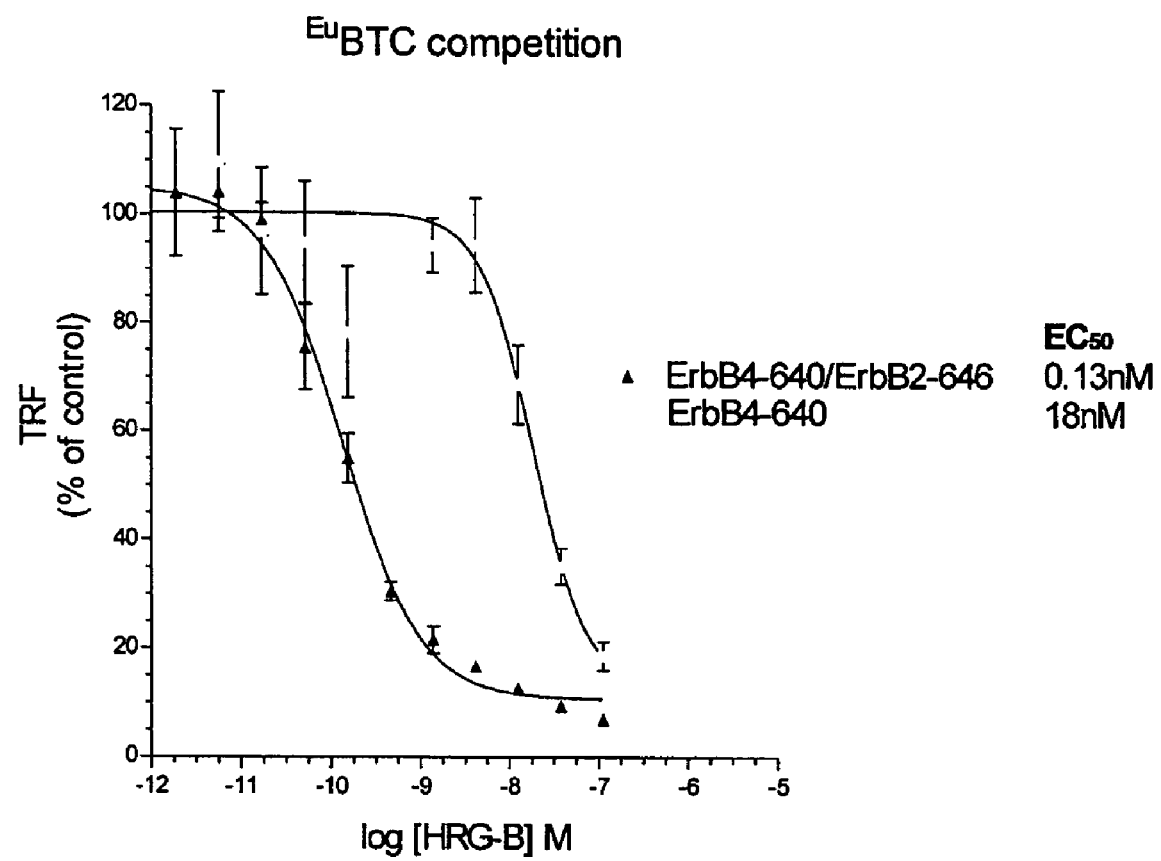

FIG. 9 Relative affinities of full-length ErbB4 ectodomain-Fc fusion homodimers and ErbB2/4 full-length ectodomain heterodimers for β-heregulin. Human 293T fibroblasts were transiently transfected with a mammalian expression vector encoding the full-length ErbB4 ectodomain-Fc fusion alone, or with vectors encoding both full-length ErbB2 and ErbB4 ectodomain-Fc fusion proteins. Supernatants were harvested and recombinant receptors immobilized by incubation in wells of a 96-well Lumitrac plate (Nunc) that had been pre-coated with protein G. Competition binding studies were performed with Europium-labelled betacellulin (BTC) as trace and increasing concentrations of unlabelled β-heregulin (Sigma). After incubation overnight at 4° C., the wells were washed and the bound trace measured by time-resolved fluorescence.

Figure 10:
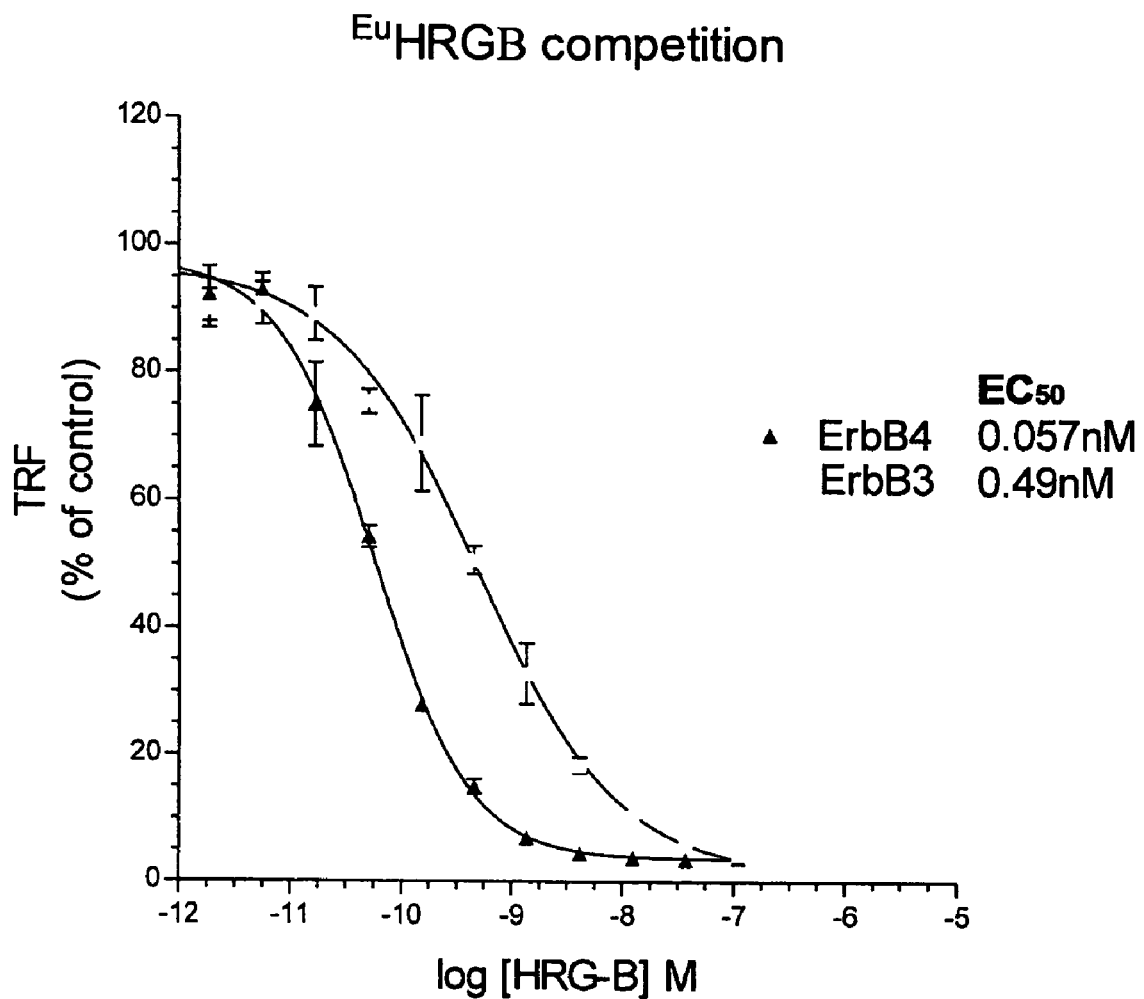

FIG. 10 Relative affinities of truncated ErbB3 ectodomain-Fc and ErbB4 ectodomain-Fc fusion protein homodimers for β-heregulin. Human 293T fibroblasts were transiently transfected with a mammalian expression vector encoding either the truncated ErbB3 ectodomain-Fc fusion protein, or with a vector encoding the truncated ErbB4 ectodomain-Fc fusion protein. Supernatants were harvested and recombinant receptors immobilized by incubation in wells of a 96-well Lumitrac plate (Nunc) that had been pre-coated with protein G. Competition binding studies were performed with Europium-labelled β-heregulin ($^{Eu}$HRGβ) as trace and increasing concentrations of unlabelled HRGβ (Sigma). After incubation overnight at 4° C., the wells were washed and the bound trace measured by time-resolved fluorescence.

DETAILED DESCRIPTION OF THE INVENTION

When used herein the term "EGFR" is intended to encompass members of the EGF receptor family such as ErbB1 (also known as the EGF receptor), ErbB2, ErbB3 and ErbB4. In general, EGF receptor family molecules show similar domain arrangements and share significant sequence identity, preferably at least 40% identity.

Figure 1A:
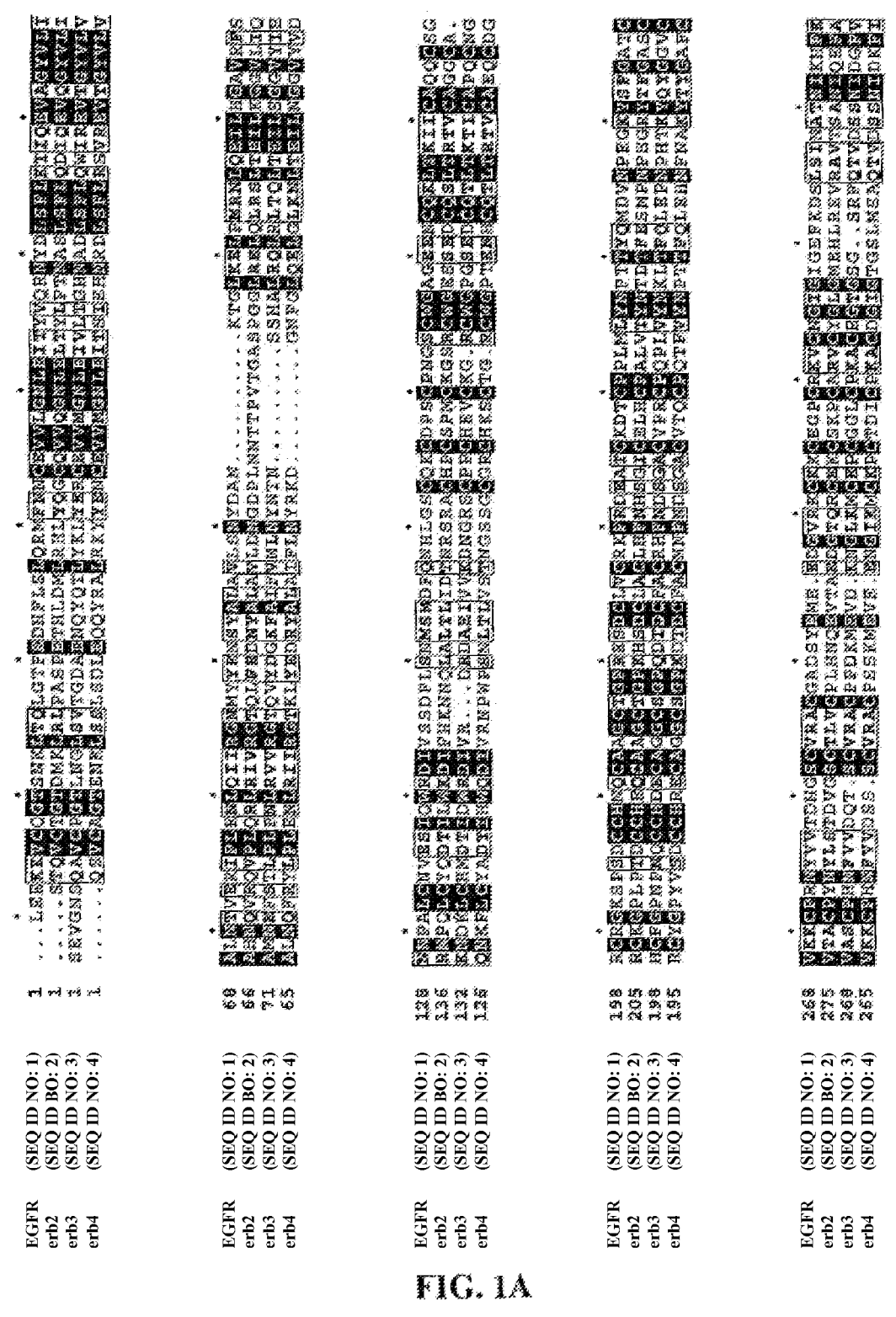
Figure 1B:
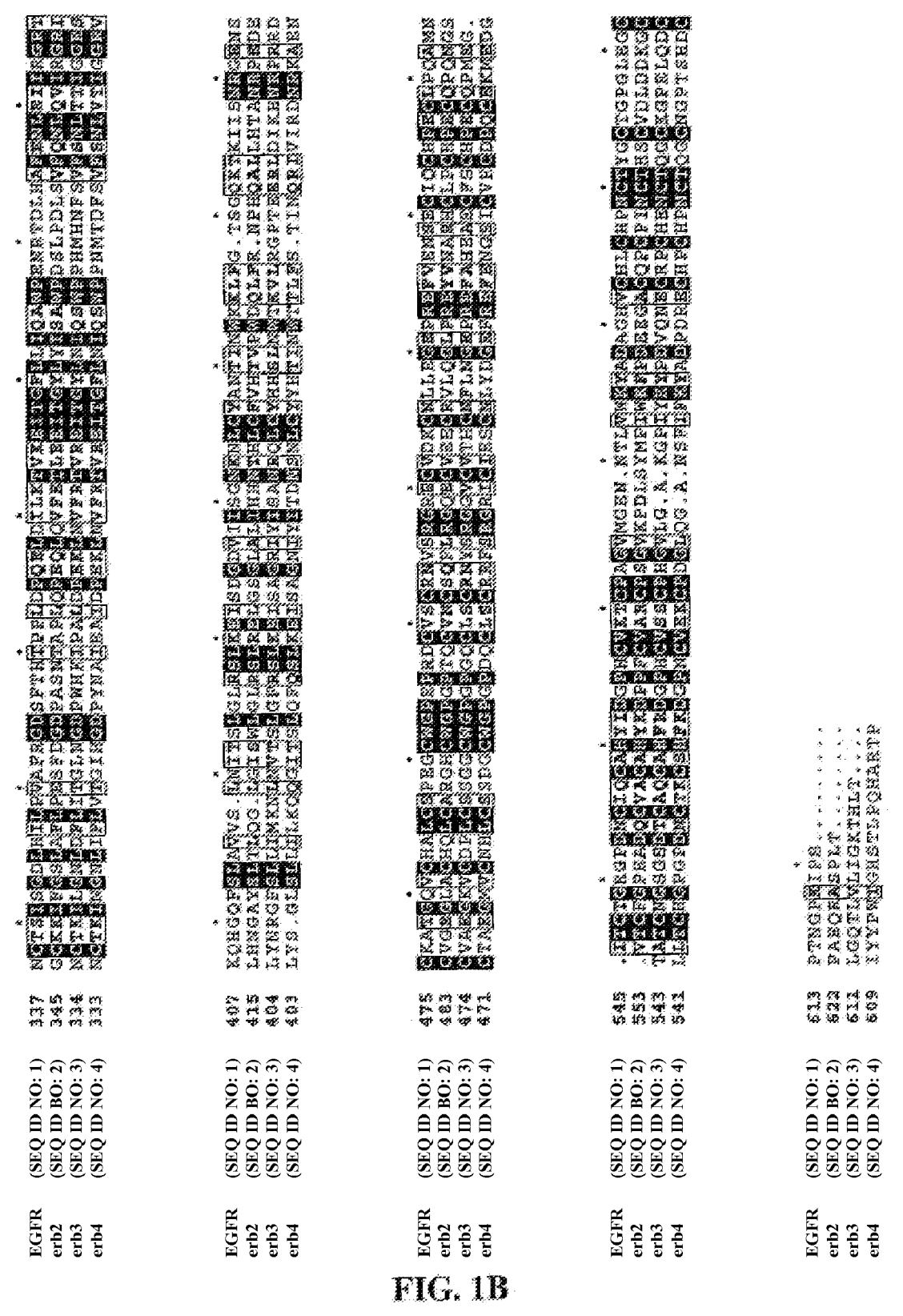

When used herein, the phrase "full length EGFR ectodomain" refers to the ectodomain consisting of residues 1-621 of ErbB1 or equivalent residues of other members of the EGF receptor family. The amino acid sequence of the full length ectodomain has been previously described (13). The full length ectodomain contains four sub-domains, referred to as L1, CR1, L2 and CR2, where L and CR are acronyms for large and cys-rich respectively. FIGS. 1A and 1B show a sequence alignment of the full length ectodomains of ErbB1, ErbB2, ErbB3 and ErbB4.

The CR2 sub-domain of ErbB1, ErbB3 and ErbB4 consists of the following seven modules joined by linkers of 2 or 3 amino acid residues and bounded by cysteine residues as follows:

|  | ErbB1 | ErbB2 | ErbB3 | ErbB4 |
| --- | --- | --- | --- | --- |
| First module | 482-499 | 490-507 | 481-498 | 478-495 |
| Second module | 502-511 | 510-519 | 501-510 | 498-507 |
| Third module | 515-531 | 523-539 | 514-530 | 511-527 |
| Fourth module | 534-555 | 542-563 | 533-554 | 530-552 |
| Fifth module | 558-567 | 566-575 | 557-566 | 555-564 |
| Sixth module | 571-593 | 579-602 | 570-591 | 568-589 |
| Seventh module | 596-612 | 605-621 | 594-610 | 592-608 |

The results presented herein show that deletions in the CR2 region of the EGFR ectodomain unexpectedly increase binding affinity of the ectodomain for EGF and/or TGF-α. In light of this information, a person skilled in the art would be able to readily generate a number of candidate truncated ectodomains and screen these candidates for increased ligand affinity and for therapeutic potential.

For example, truncated ectodomains may be prepared by recombinant DNA technology as described herein or as described previously (8). Alternatively, truncated ectodomains may be prepared by subjecting the full length ectodomain or full length receptor to limited proteolysis as described previously (9).

Binding affinity and inhibitor potency may be measured for candidate truncated ectodomains using biosensor technology.

Truncated EGFR ectodomains of the invention may be in a substantially isolated form. It will be understood that the protein may be mixed with carriers or diluents which will not interfere with the intended purpose of the protein and still be regarded as substantially isolated. A truncated ectodomain of the invention may also be in a substantially purified form, in which case it will generally comprise the protein in a preparation in which more than 90%, e.g. 95%, 98% or 99% of the protein in the preparation is a protein of the invention.

In the context of the present invention, the amino acid sequence of the truncated EGFR ectodomain may be modified provided that the modification does not adversely affect the binding affinity of the truncated ectodomain for at least one EGFR ligand. For example, modified ectodomains may be constructed by making various substitutions of residues or sequences or deleting terminal or internal residues or sequences not needed for binding activity. Generally, substitutions should be made conservatively; i.e., the most preferred substitute amino acids are those having physiochemical characteristics resembling those of the residue to be replaced. Similarly, when a deletion or insertion strategy is adopted, the potential effect of the deletion or insertion on biological activity should be considered. In order to preserve the biological activity of the truncated ectodomains, deletions and substitutions will preferably result in homologous or conservatively substituted sequences, meaning that a given residue is replaced by a biologically similar residue. Examples of conservative substitutions include substitution of one aliphatic residue for another, such as Ile, Val, Leu, Met or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Moreover, particular amino acid differences between human, murine and other mammalian EGFRs is suggestive of additional conservative substitutions that may be made without altering the essential biological characteristics of the truncated EGFR ectodomains.

Modifications encompassed by the present invention also include various structural forms of the primary protein which retain binding affinities. Due to the presence of ionizable amino and carboxyl groups, for example, a truncated ectodomain may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Other modifications within the scope of this invention include covalent or aggregative conjugates of the truncated ectodomain with other proteins or polypeptides, such as by synthesis in recombinant culture as N-terminal or C-terminal fusions. For example, the conjugated polypeptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast I-factor leader). Truncated EGFR ectodomain fusions may comprise peptides added to facilitate purification or identification of the truncated ectodomain (e.g., poly-His) or to enhance stability or delivery of the ectodomain in vivo.

The truncated EGFR ectodomains of the present invention may also be fused to the constant domain of an immunoglobulin molecule. For example, a recombinant chimeric antibody molecule may be produced having truncated EGFR ectodomain sequences substituted for the variable domains of either or both of the immunoglubulin molecule heavy and light chains and having unmodified constant region domains. This may result in a single chimeric antibody molecule having truncated EGFR ectodomains displayed bivalently. Such polyvalent forms of the truncated EGFR ectodomain may have enhanced binding affinity for EGFR ligands. Details relating to the construction of such chimeric antibody molecules are disclosed in WO 89/09622 and EP 315062.

As TGFα exists as a membrane bound form, the truncated ectodomains of the present invention may be used to target compounds to cancer cells. Accordingly, truncated EGFR ectodomain fusions may comprise compounds useful in the diagnosis or treatment of cancer cells such as drugs, isotopes or toxins.

Truncated EGFR ectodomain derivatives may also be obtained by cross-linking agents, such as M-maleimidobenzoyl succinimide ester and N-hydroxysuccinimide, at cysteine and lysine residues. The truncated ectodomains may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, the truncated ectodomain may be used to selectively bind (for purpose of assay or purification) anti-EGFR antibodies or EGF.

It may also be desirable to use derivatives of the ectodomains of the invention that are conformationally constrained. Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure.

It will be appreciated that the truncated EGFR ectodomains of the present invention may be used as immunogens, reagents in receptor-based immunoassays, or as binding agents for affinity purification procedures of EGF or other binding ligands.

Truncated EGFR ectodomains may be tested for their ability to modulate receptor activity using a cell-based assay incorporating a stably transfected, EGF-responsive reporter gene (10). The assay addresses the ability of EGF to activate the reporter gene in the presence of novel ligands. It offers a rapid (results within 6-8 hours of hormone exposure), high-throughput (assay can be conducted in a 96-well format for automated counting) analysis using an extremely sensitive detection system (chemiluminescence). Once candidate compounds have been identified, their ability to antagonise signal transduction via the EGF-R can be assessed using a number of routine in vitro cellular assays such as inhibition of EGF-mediated cell proliferation. Ultimately, the efficiency of truncated EGFR ectodomains as tumour therapeutics may be tested in vitro in animals bearing tumour isografts and xenografts as described (11, 12).

Truncated EGFR ectodomains of the invention (and substances identified by the assay methods of the invention) may preferably be combined with various components to produce compositions of the invention. Preferably the compositions are combined with a pharmaceutically acceptable carrier or diluent to produce a pharmaceutical composition (which may be for human or animal use). Suitable carriers and diluents include isotonic saline solutions, for example phosphatebuffered saline. The compositions may be formulated, for example, for parenteral, intramuscular, intravenous, subcutaneous, intraocular, oral or transdermal administration. Typically, each protein may be administered at a dose of from 0.01 to 30 mg/kg body weight, preferably from 0.1 to 10 mg/kg, more preferably from 0.1 to 1 mg/kg body weight.

The routes of administration and dosages described are intended only as a guide since a skilled practitioner will be able to determine readily the optimum route of administration and dosage for any particular patient and condition.

In view of the ability of the truncated EGFR ectodomains of the present invention to bind strongly to EGFR ligands, the truncated ectodomains will be useful in diagnostic assays for EGFR ligands, as well as in raising antibodies to the EGFR for use in diagnosis and therapy. In addition, purified truncated EGFR ectodomains may be used directly in therapy to bind or scavenge EGFR ligands, thereby providing means for regulating the activities of these ligands. In particular, truncated EGFR ectodomains of the present invention may be administered for the purpose of inhibiting EGF-dependent responses.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, the term "consisting essentially of" is intended to exclude elements which would materially affect the properties of the claimed composition.

The invention will now be described in further detail with reference to the following non-limiting Examples.

Experimental Details

Materials and Methods

Construction of plasmids used for the expression of truncated forms of hErbB1 ectodomain. The plasmid pErbB1, used in the construction of truncated hErbB1 cDNAs, comprises nucleotides 167-3970 of hErbB1 (13) in the multiple cloning site of plasmid pUC18. Coding is in the opposite sense to the LacZ α peptide, and the insertion is downstream of the XbaI site of pUC18. This plasmid was used later in excision of the truncated constructs for insertion into the mammalian expression vector pEE14 (14).

Construction of pErbB1476. An initial plasmid containing nucleotides 167-3150 of hErbB1 was constructed by ligation of a XbaI/NsiI fragment from pEGFR and XbaI/PstI-cut pBluescript KS+. From this plasmid, a 4 kbp fragment BbsI/Bg/II fragment (containing all of pBluescript KS+ and nucleotides 167-1150 and 2951-3150 of EGFR) and a 528 bp BbsI/PvuII fragment (nucleotides 1151-1679) were ligated with a 70 bp PCR-derived PvuII and Bg/II fragment, encoding amino acids 474-476 of hEGFR, an enterokinase cleavage site and a c-myc epitope tag to facilitate purification. The 70 bp PCR cassette was produced using a similar previous construct (15) as template. A plasmid for mammalian cell transfection, pErbB1476, was constructed from this plasmid by ligation of a 1.6 kbp XbaI/EcoRV fragment with XbaI/SmaI-cut pEE14.

Construction of pErbB1501 and pErbB1513. In each construction PCR was used with three oligonucleotides to produce a fragment of hEGFR cDNA (nucleotides 1121 to 1760 or 1121 to 1797 respectively), followed by a sequence encoding an enterokinase cleavage site, a c-myc epitope tag and a termination codon. The upstream primer in PCR corresponded to an arbitrary choice of nucleotides 1121-1140 of hEGFR cDNA, while two overlapping downstream primers were used to construct additional sequence adjacent to nucleotide 1760 or 1797 respectively. The PCR products were cloned using the pCR-Script vector (Stratagene). In each case this allowed an ApaI fragment harbouring the newly constructed sequence beginning at nucleotide 1738 of hErbB1, to be excised for subsequent insertion into the large ApaI fragment of pEGFR (which included the entire pUC18 sequence with hErbB1 cDNA to nucleotide 1737), in order to prepare a plasmid encoding a truncated hEGFR with XbaI restriction sites adjacent to the coding sequence. From these pUC18-based plasmids the fragments harbouring the truncated hErbB1 cDNAs were excised by XbaI digestion, and inserted into plasmid pEE14 at the XbaI site to prepare plasmids pErbB1501 and pErbB1513 respectively for mammalian cell transfection.

Mutagenesis. The 1.7 kbp fragment harbouring the truncated hErbB1 cDNA of pEGFR501 was introduced into M13 mp18 (16) for mutagenesis. Oligonucleotide-directed in vitro mutagenesis, using the USB-T7 Gen™ in vitro mutagenesis kit, was employed to produce three single site mutants of the truncated human sErbB1501 ectodomain, with residues Glu367, Gly441 and Glu472 respectively mutated to Lys to match the corresponding residues in chicken ErbB1 (4). Clones incorporating the mutations were identified by colony hybridisation (17) using $^{32}$P-labelled mutagenic oligonucleotide as a probe, and the mutations were confirmed by DNA sequence analysis (18). Vehicles for mammalian cell expression were generated for each mutant by excising the 1.7 kbp fragment harbouring the mutated sErbB1501 cDNA from M13 RF-DNA by XbaI digestion and inserting it into plasmid pEE14 (16) at the XbaI site.

Vector assembly for production of ErbB1, ErbB3 and ErbB4 Fc fusion proteins. DNA templates encoding a number of full-length and truncated ectodomain fragments for ErbB1, ErbB3 and ErbB4, fused in frame with a genomic fragment coding for the human IgG1 Fc region together with an N-terminal spacer peptide and a C-terminal epitope tag, were generated using standard molecular techniques. DNA templates were assembled in plasmid expression vectors, enabling transcription and the subsequent translation of the encoded fusion protein following transfection into mammalian cells.

Cell Culture, DNA Transfection and Protein Analysis. For transient transfection assays, human 293T fibroblasts maintained in DMEM plus 10% fetal calf serum (FCS) were transfected with plasmid DNA using FuGENE (Roche Molecular Biochemicals, Sydney, NSW) according to the manufacturer's instructions. Supernatants were harvested 48 h after transfection, and cell lysates were prepared in NP-40 lysis buffer. To characterise secreted EGFR mutants, aliquots of supernatant and lysate were immunoprecipitated with a monoclonal antibody (9E10) to the c-myc tag, or with Mab 225 (HB-8508, American Type Culture Collection), a conformationally dependent monoclonal antibody recognising the extracellular domain of the hErbB1 (19). Immune complexes were collected on Protein A-Sepharose beads (Zymed Laboratories, Bioscientific Pty. Ltd., Gymea, NSW), fractionated by SDS polyacrylamide gel electrophoresis (10% gel) and transferred to nitrocellulose membranes. Truncated hEGFR ectodomains and mutants were identified by probing membranes with horseradish peroxidase (HRP)-conjugated Mab9E10 (Roche), followed by chemilumiscent detection with Pierce Super Signal substrate.

Stable cell lines expressing ErbB1501 were established in the Lec8 mutant cell line from CHOK (7) using glutamine synthetase as a selectable marker (15). Supernatants from methionine sulfoximine (MSX)-resistant cell colonies were screened for secreted receptor by biosensor analysis (see below) or by dot blotting onto nitrocellulose and probing with HRP-Mab9E10. A single cell line was selected for cloning by limiting dilution.

Lec8 cells expressing ErbB1501 protein were cultured in a Celligen Plus bioreactor (New Brunswick Scientific, New Jersey, USA) using 70 g Fibra-Cell Disks carriers with 1.7 L working volume. Continuous perfusion culture using glutamine-free DMEM/F12 medium supplemented with non-essential amino acids, nucleosides and 10% FCS was maintained for 6 weeks. Selection pressure was maintained with 25 µM MSX for the duration of the fermentation. Perfusion rate was adjusted as required to ensure a residual glucose level of 1.0-1.5 g/L, with a corresponding lactate concentration of 2.0-2.3 g/L.

HEK 293T cells were transfected with plasmid DNA encoding ErbB1, ErbB3 and ErbB4 Fc fusion proteins complexed with FuGENE (Boehringer) 24 hours after seeding into six-well plates. Twenty four hours later, the culture medium was replaced with serum-free medium, and supernatant harvested 24-48 hours later.

Purification of Truncated EGFR Ectodomains. For biosensor and AUC analyses, conditioned medium containing the sEGFR truncated proteins (4 L) was adjusted to pH 8.0 with Tris-HCl (Sigma) containing sodium azide (0.02% (w/v)) (TBSA), and particulates removed by centrifugation prior to recovery of c-myc-tagged protein by affinity purification at 4° C. on a column of monoclonal antibody 9E10 covalently-bound to agarose, using peptide elution (15). Eluted protein was further purified by size exclusion chromatography on Superdex 200 (HR 10/30, Amersham Pharmacia Biotech) at room temperature using TBSA buffer at a flow rate of 0.8 ml/min. Protein was detected by absorbance at 280 nm.

BIAcore Binding Assays. Protein-protein interactions were monitored in real time on an instrumental optical biosensor using surface plasmon resonance detection (BIAcore 2000 or 3000, BIAcore, Uppsala, Sweden). Recombinant hEGF or hTGF-I (Gropep, Adelaide, Australia) were purified immediately prior to immobilisation by micropreparative RP-HPLC using a SMART system (Amersham Pharmacia Biotech) as described previously (20). The proteins were immobilised onto the biosensor surface using amine coupling chemistry (N-hydroxysuccinimide and N-ethyl-N'-dimethylaminopropyl-carbodiimide) at a flow rate of 4 µl/min. Typically 100-200 RU were immobilised equivalent to 0.1-0.2 ng/mm$^2$ (20). Automated targeting of immobilisation levels was achieved using the BIAcore 3.1 control software (21).

Prior to analysis, ErbB1621 (23), ErbB1501 and the ErbB1501 mutant samples were characterised by micropreparative size exclusion chromatography (Superose 12 3.2/30, Amersham Pharmacia Biotech) to ensure size homogeneity (20) and pooled fractions were diluted in BIAcore buffer (HBS: 10 mM Hepes pH 7.4 containing 3.4 mM EDTA, 0.15 mM NaCl and 0.005% (v/v) Tween 20) to the appropriate concentration. Typically, samples (30 µl) at concentrations of 10-1000 nM were injected sequentially over the sensor surfaces at a flow rate of 5 or 10 µl/min. Following completion of the injection phase, dissociation was monitored in BIAcore buffer at the same flow rate. The sensor surface and sample blocks were maintained at 25° C. Bound receptor was eluted, and the surface regenerated between injections, using 40 µl of 10 mM HCl. This treatment did not denature hEGF or hTGF-α immobilised onto the sensor surface, as shown by equivalent signals on re-injection of receptor.

Kinetic rate constants (ka, kd) were determined using the BIAevaluation 3.02 software (BIAcore, http//www.biacore-.com/products/eval3.html) as described previously (22), or by global analysis using CLAMP (23, 24). Equilibrium binding constants (KA, KD) were determined by direct non-linear least squares analysis of the binding data using an equation defining steady state equilibrium (KA*Conc*Rmax/(KA*Conc*n); BIAevaluation 3.1). The data was also plotted in Scatchard format (Req/nC versus Req, where Req is the biosensor response at equilibrium, n is the valency and C is the concentration) (25).

Analytical Ultracentrifugation. Experiments were performed using a Beckman XL-A analytical ultracentrifuge (Beckman Coulter, Inc., Fullerton, Calif.) equipped with absorption optics, using an An60-Ti rotor with cells containing quartz windows, as described previously (23). Centrifugation experiments were conducted at 20° C. using a sample volume of 100 µl. Equilibrium sedimentation distributions obtained at 12,000 and 20,000 rpm, were monitored at 280 or 290 nm and analysed using the program SEDEQ1B (26). The partial specific volume of EGF was taken as 0.71 ml/g (23).

Chemical Cross Linking. Chemically cross-linked ErbB1501 dimers were generated by the incubation of sEGFR501 (5 µM) with mEGF (20 µM) in 20 mM HEPES pH7.4 containing 150 mM NaCl for 1 h at room temperature followed by the addition of bis(sulfosuccinimidyl)suberate (BS3, Pierce, Rockford, Ill., USA) to a final concentration of 0.5 mM and incubation for a further 30 min. The reaction was terminated by the addition of Tris-HCl buffer (pH 7.5) to a final concentration of 10 mM. Monomer-dimer separation was achieved on Novex non-reducing SDS-PAGE gels (10%). Proteins were transferred onto poly(vinyl difluoride) (PVDF) membranes (Bio-Rad, Hercules, Calif., USA) and identified by incubation with anti-EGFR Mab528 (19) (0.5 µg/ml) followed by horseradish-peroxidase labelled goat anti-mouse IgG (Bio-Rad) and ECL detection (Amersham Pharmacia Biotech).

Cell Proliferation Assays. BaF/3ERX cells, a cell line derived from BaF/3 cells transfected with human EGFR (obtained from Ludwig Institute for Cancer Research, Melbourne) were washed three times to remove residual IL-3 and resuspended in RPMI 1640+10% FCS. Cells were seeded into 96 well plates using a Biomek 2000 robotic autosampler (Beckman) at $2 \times 10^4$ cells per 200 µl and incubated for 4 h at 37° C. in 10% $CO_2$. Appropriate concentrations of ErbB1501 or ErbB1621 or the anti-EGFR monoclonal antibody Mab528, were added to the first titration point and titrated in two-fold dilutions across the 96 well plate in duplicate with or without a constant amount of mEGF (207 pM). $^3$H-Thymidine (0.5 µCi/well) was added and the plates were incubated for 20 h at 37° C. in 5% $CO_2$. The cells were then lysed in 0.5 M NaOH at room temperature for 30 min before harvesting onto nitrocellulose filter mats using an automatic harvester (Tomtec, Connecticut, USA). The mats were dried in a microwave, placed in a plastic counting bag and scintillant (10 ml) was added. $^3$H-Thymidine incorporation was determined using an automated beta counter (1205 Betaplate, Wallac, Finland).

Ligand binding assays. The wells of a 96-well Lumitrac 600 plate (Greiner) were coated with protein G (2 ug/ml in 10 mM sodium citrate buffer, pH 9.6; Sigma). The wells were subsequently blocked with 0.5% ovalbumin/Tris-buffered saline (TBS). Culture supernatant from cell transfectants was added to the wells and incubated overnight at 4° C. to allow the binding of Fc fusion proteins to protein G. Wells were washed and a cocktail of a fixed concentration of Europium (Eu)-labelled ligand (EGF or HRGβ, depending on the fusion protein), together with varying concentrations of unlabelled competitor ligand, added to each well in ligand-binding buffer. After incubation at room temperature, wells were aspirated, washed in TBS plus 0.05% Tween-20, and Enhancement Solution (Perkin-Elmer) added to each well for 20 minutes. Samples were then assayed for time-resolved fluorescence (TRF) using a Wallac Victor2 1420 Multilabel Counter.

EXAMPLE 1

Production and Purification of Truncated EGFR Ectodomains

Preliminary analysis of conditioned media from cells transiently expressing ErbB1476, ErbB1501 and ErbB1513 showed that only the latter two truncated receptors gave detectable binding to hEGF immobilised on the BIAcore biosensor. Stably transfected Lec8 cells expressing ErbB1501, were generated and used to produce truncated receptor protein at a yield of ~1.8 mg/L of fermentation medium for physical-chemical characterisation.

ErbB1501 purified from a Mab9E10 anti-c-myc peptide affinity column using peptide elution showed a single symmetrical peak on size exclusion chromatography (apparent molecular mass of ~80 kDa) and migrated as a single band of ~70 kDa on SDS-PAGE under reducing conditions. ErbB1501 gave a unique expected sequence, LEEKKVXQGT (13) on N-terminal amino acid sequence analysis, the X at cycle 7 being due to the presence of a disulphide-bonded cysteine residue at that position. The apparent molecular mass of approximately 70 kDa on SDS-PAGE is due to the residual glycosylation reported for the glycosylation defective Lec 8 cells (33) since the calculated mass of human ErbB1501 apo-protein is ~57.5 kDa. There are eight potential N-linked glycosylation sites in ErbB1501 (13) and incubation of ErbB1501 with peptide-N-glycosidase (PNG'ase) at 37° C. resulted in the generation of a major band migrating on SDS-PAGE with an apparent molecular mass of 57-58 kDa (data not shown). We have shown previously using BIAcore analysis that removal of carbohydrate using PNGase does not affect binding of sEGFR621 to the immobilised ligand, in agreement with the concept that glycosylation is required for correct processing but not for biological activity. All subsequent experiments were carried out using the ~70 kDa ErbB1501.

EXAMPLE 2

Affinity Binding of sEGFR501

The BIAcore biosensor was used to determine both the rate and equilibrium binding constants for the interaction between ErbB1501 and hEGF or hTGF-α. Full length ectodomain (ErbB1621) was used as a positive control for the surface reactivity, since this interaction has been studied in detail previously (23, 27).

Figure 2:
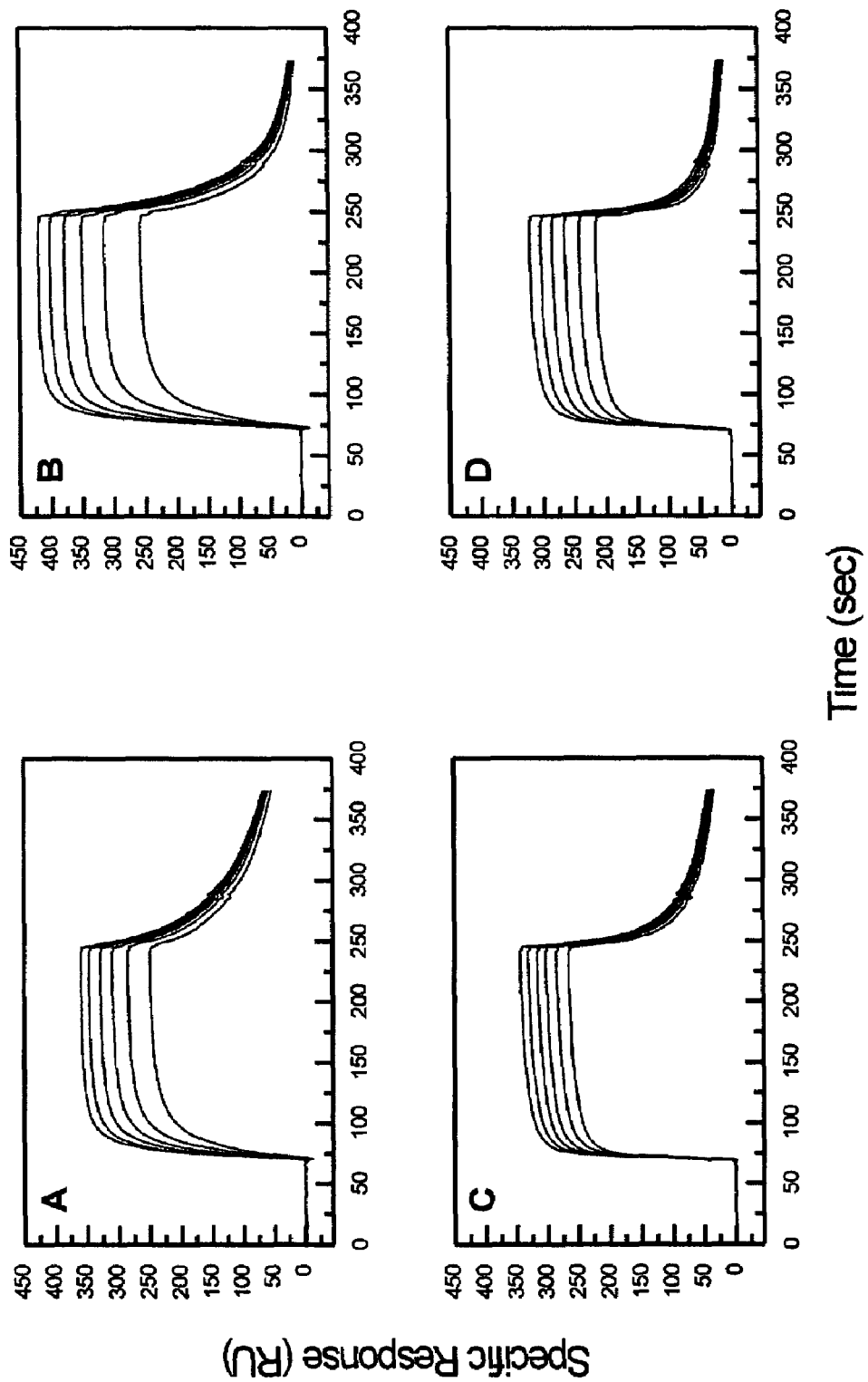
FIG. 2: BIAcore analysis of the interactions between ErbB1501 and ErbB1621 with immobilised hEGF or hTGF-α. (A): ErbB1-501 (140, 120, 100, 80, 60 and 40 nM) was passed over immobilised hEGF (160 RU immobilised). Samples (30 TI) were injected at a flow rate of 10 TI/min. (B): ErbB1-501 was passed over immobilised hTGF-I (132 RU immobilised). Experimental details were as in panel A. (C): sEGFR621 (1000, 900, 800, 700, 600 and 500 nM) was passed over immobilised hEGF. (D): ErbB1-621 (concentrations as for panel C) was passed over immobilised hTGF-I. The operating temperature was 25° C. At the end of the injection phase, dissociation was monitored with buffer alone flowing over the sensor surface. The surface was regenerated between samples using 10 mM HCl. The signal obtained when the sample was passed over a parallel blank channel has been subtracted electronically to give the specific response.
Figure 3:
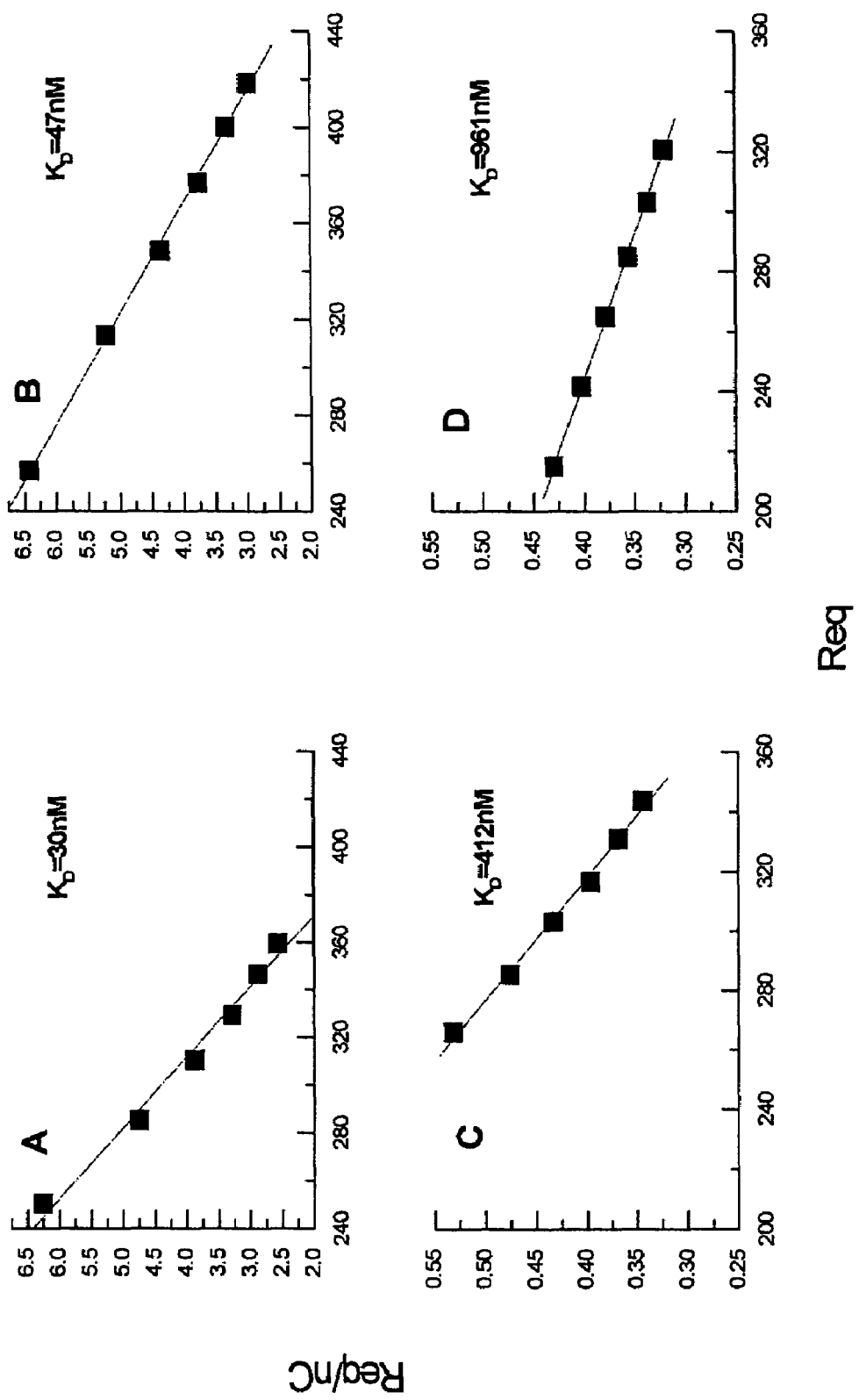
FIG. 3: Scatchard analysis of equilibrium binding data. The dissociation constant (KD=1/KA) was calculated from the equilibrium binding response obtained in FIG. 2 by plotting the data in Scatchard format (Req/nC versus Req; see Experimental Procedures). The slope of the linear fit to the data gives KA. (A): ErbB1501 versus hEGF; (B): ErbB1501 versus hTGF-I;. (C): ErbB1621 versus hEGF; (D): ErbB1621 versus hTGFI.

Representative sensorgrams for the interaction between ErbB1501 or ErbB1621 and hEGF or TGF-α are shown in FIG. 2. Visual inspection revealed that the curves approached equilibrium over the concentration ranges tested. Additionally, the hTGF-α sensorgrams appeared to show more rapid, and virtually complete, dissociation. Thermodynamic analysis of the equilibrium binding data in Scatchard format (FIG. 3) indicated $K_D$ values of 30 and 47 nM (correlation coefficient R=0.993 and 0.999 respectively) for the interactions between ErbB1501 and immobilised hEGF or hTGF-α and 412 and 961 nM (R=0.997 and 0.999 respectively) for the corresponding interactions with ErbB1621. The values obtained by Scatchard transformation were also confirmed by direct non-linear least squares analysis of the binding data (data not shown) using an equation defining steady state equilibrium (KA*Conc*Rmax/(KA*Conc*n); BIAevaluation 3.1). Using this analysis, $K_D$ values of 32 and 46 nM were calculated for the interaction between ErbB1501 and immobilised hEGF and hTGF-α respectively and 570 and 959 nM for the interaction between full-length ectodomain (ErbB1621) and immobilised hEGF and hTGF-α. The values obtained with ErbB1621 were in good agreement with those reported previously (23), confirming the surface viability.

The individual rate constants were determined from those parts of the curves where first order kinetics appeared to be operative (27, 28), and the corresponding dissociation constants calculated (Table 1). Again, there was good agreement between the $K_D$ values calculated in this manner and those obtained from the equilibrium binding data. It is interesting to note that the binding curves obtained with both ErbB1501 and ErbB1621 for hTGF-α appeared to be better fitted to a 1:1 model than the corresponding data for the hEGF surface (as suggested by the virtually complete dissociation).

TABLE 1

Comparative kinetic data for ligand binding by truncated and full-length EGFR ectodomains.

| Interaction | $k_a$ (M$^{-1}$s$^{-1}$) × 10$^{-5}$ | $k_d$ (s$^{-1}$) | $K_D$ (nM) |
|---|---|---|---|
| ErbB1501/EGF | 10-17 | 0.02 | 13-21 |
| ErbB1501/TGF-α | 9.3-10.5 | 0.04 | 35-40 |
| ErbB1621/EGF | 2.9-4.8 | 0.08 | 180-300 |
| ErbB1621/TGF-α | 0.7-1.0 | 0.08 | 840-1320 |

EXAMPLE 3

Antagonist Activity of ErbB1501

Figure 4:
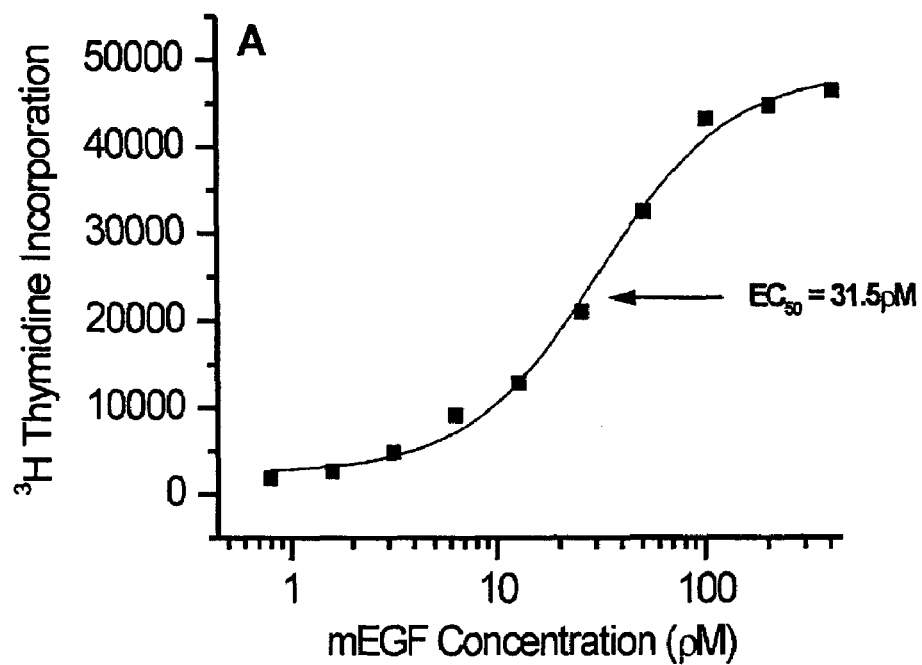
FIG. 4: Inhibition of EGF-stimulated cell mitogenesis by ErbB1501. (A): The stimulation of $^3H$-thymidine incorporation by BaF/3ERX cells using serial dilutions of mEGF. The data was fitted by a sigmoidal function (–) to determine the $EC_{50}$. (B): Inhibition of the mitogenic response of BaF/3ERX cells stimulated with mEGF (207 pM) by: ErbB1501 (■-■), ErbB1621 (●-●) or anti-EGFR antibody Mab528 (▲-▲). Each point was assayed in triplicate. Error bars are shown.
Figure 4:
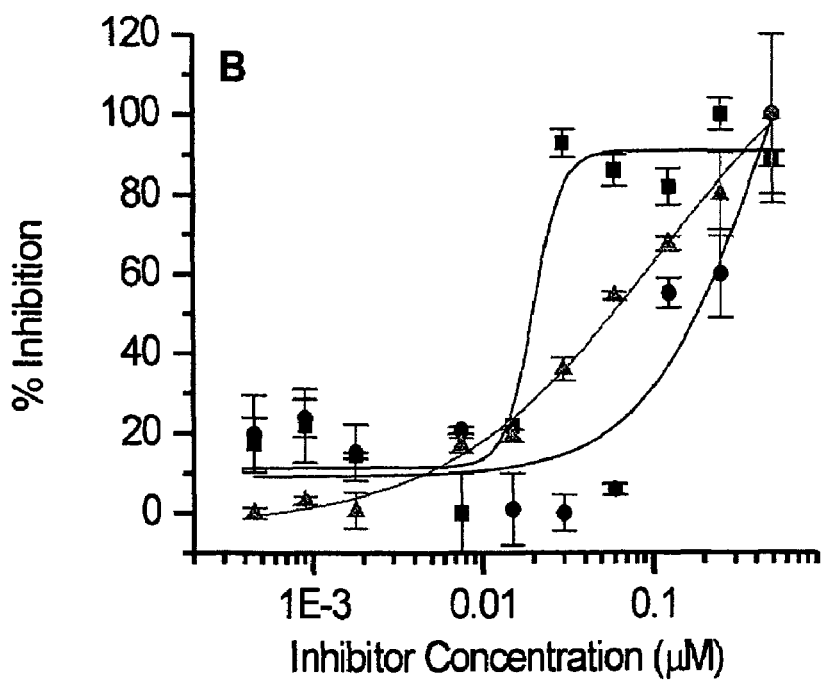

The observation that ErbB1501 bound EGF with high affinity prompted us to test whether ErbB1501 would act as a competitive inhibitor for the mitogenic stimulation of EGFR in a cell-based assay using the BaF/3ERX cell line. This cell line responds to mEGF with an EC50 of approximately 30 pM (FIG. 4A). The competition assay (FIG. 4B) used a constant concentration of mEGF (207 pM), which causes maximal stimulation (FIG. 4A), and varying levels (0.00045-0.5 µM) of ErbB1501, ErbB1621 or the neutralising anti-EGFR monoclonal antibody Mab528 raised against epidermal growth factor receptors on a human epidermoid carcinoma cell line, A431 (19). This antibody has been shown to prevent the growth of A431 cell xenografts, bearing high numbers of EGF receptors, in nude mice. The ErbB1501 (IC50=0.02 µM) was almost 10 fold more potent than the full-length ectodomain (IC50=0.15 µM) and approximately 3-fold more potent than the Mab528 anti-EGFR monoclonal antibody (IC50=0.06 µM).

EXAMPLE 4

Dimerisation of sEGFR501

Figure 5:
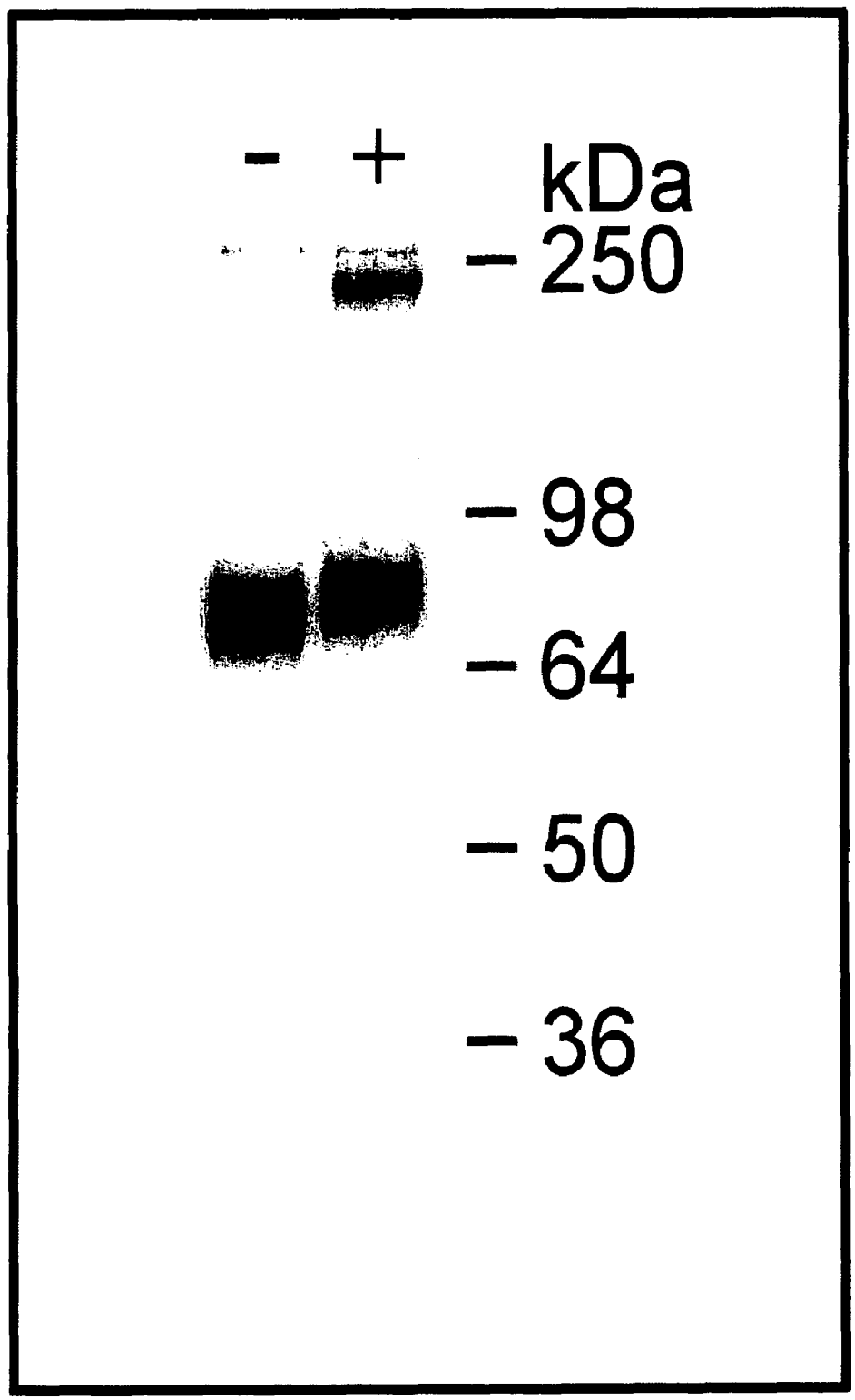
FIG. 5: Covalent cross-linking of ErbB1501 dimers after incubation with mEGF. sEGFR501 (5 μM) was incubated with (+) or without (−) mEGF (20 μM) in 20 mM HEPES (pH7.4) containing 150 mM NaCl for 1 h at room temperature followed by the addition of bis(sulfosuccinimidyl)suberate (BS3, Pierce, Rockford, Ill., USA) to a final concentration of 0.5 mM and incubation for a further 30 min. The reaction was terminated and the degree of dimer formation was monitored by SDS-PAGE and immunoblotting with anti-EGFR Mab528

Chemical cross-linking revealed that ErbB1501 formed dimeric complexes in the presence of ligand. In the presence of 20 µM mEGF, a single high molecular weight species (apparent Mr 180,000 Da) was formed after chemical cross-linking which was not detectable when the cross-linking was attempted in the absence of ligand (FIG. 5). Western blotting was employed to confirm the authenticity of the bands observed, but similar data were obtained with silver or Coomassie blue staining. In addition, size exclusion chromatographic analysis of the reaction mixture, using a TSK G2000SW column developed with a mobile phase of PBS at a flow rate of 0.25 ml/min, showed a peak of apparent Mr 158,000 which corresponded to dimer (data not shown). Similar results have previously been obtained with ErbB1621.

Analytical ultracentrifugation showed that the EGF binding sites on ErbB1501 were saturated at an equimolar ratio of ligand and receptor leading to the formation of a 2:2 EGF/ErbB1501 complex (FIG. 6). The data for 20 TM EGF alone (FIG. 6A) indicate a single solute of molecular weight 5,980 Da, in good agreement with the value calculated from the amino acid composition (6,040 Da). The molecular weight (65,600 Da) and partial specific volume (0.71 ml/g) determined for 10 TM ErbB1501 alone was calculated from the sedimentation equilibrium distribution (FIG. 6A) and is based on the known amino acid composition and a calculated value of 12% (w/w) for the carbohydrate composition.

Sedimentation equilibrium data for a mixture of EGF (20 μM) and ErbB1501 (10 μM) was analyzed assuming two species (FIG. 6A). The molecular weight of the first species was fixed at the value obtained for free EGF (6,000 Da) with the molecular weight and weight fraction of the second species used as fitting parameters. Under these conditions the molecular weight of the second species provides a good approximation to the weight-average molecular weight of ErbB1501 and its complexes. The best-fit value showed a complex of weight-average MW 106,400 Da, higher than predicted for a 1:1 complex (71,600 Da) and more consistent with the formation of a significant proportion of dimeric 2:2 EGF/ErbB1501 complex (see below).

High-speed meniscus depletion experiments were performed to determine the molar ratio required for saturation of ErbB1501 with EGF (FIG. 6B). A solution of ErbB1501 (5 μM) was titrated with EGF to determine the molar ratio at which free EGF is detectable at the meniscus. The results show that this occurs above 5 μM EGF, implying an equimolar ratio is required for saturation of the EGF binding site(s) on ErbB1501. These data, taken together with the observed weight average molecular weight of the EGF/ErbB1501 complex obtained from the equilibrium analysis (FIG. 6A), confirm that the stoichiometry of the EGF/ErbB1501 dimeric species is 2:2 not 2:1.

Sedimentation equilibrium was used for the analysis of data obtained for ErbB1501 (5 μM) in the presence of a range of EGF concentrations (FIG. 6C). The weight average molecular weight obtained for the "second" species increases rapidly as the ratio of EGF/ErbB1501 is increased to 1:1 and then tends to plateau around approximately 108,000 at ratios above 2:1 (FIG. 6C). The data in FIG. 6A could also be fitted assuming a mixture of 1:1 and 2:2 complexes with weight fractions of the monomeric and dimeric ErbB1501 complexes of 57% and 31% respectively. Similar data was obtained with ErbB1621 (23).

EXAMPLE 5

ErbB1501-441 Mutant Binding Studies

Biosensor analysis was also used to analyse the binding of the transiently expressed sEGFR501 mutants to both immobilised hEGF and hTGF-α surfaces. The presence of the mutant proteins in culture supernatants from transfected cell lines was demonstrated by both immunoblotting with the anti-EGFR monoclonal antibody, Mab 528, and biosensor analysis using Mab 528 immobilised on the surface. Culture supernatants from all cell lines showed demonstrable binding to the Mab surface (441>472=wt>367).

In preliminary experiments, the Glu367Lys mutant and the Glu472Lys mutant showed similar binding characteristics to sEGFR501 when passed over the hEGF sensor surface. The Gly441Lys mutant showed much reduced binding, even though the Mab528 surface had indicated that the Gly441 Lys mutant was present at higher concentrations than sEGFR501. Interestingly, when the same samples were passed over the parallel hTGF-α sensor surface the Gly441 Lys mutant now showed the highest binding, whilst the binding of the Glu367Lys mutant the Glu472Lys mutant and wild type ErbB1501 were again similar but lower.

For full biosensor analysis the mutant proteins present in the conditioned media from transient transfected 293T fibroblasts were concentrated and purified by a combination of affinity purification using the 9E10 monoclonal antibody and size exclusion chromatography on Superdex 200 and Superose 12. The sensorgrams obtained with the immobilised hEGF and hTGF-α surfaces (160 and 132 RU immobilised respectively) are shown in FIGS. 7A, 7B. As we had observed in the preliminary experiments, whilst the binding characteristics of the Glu367Lys and Glu472Lys mutants were essentially undistinguishable from those of ErbB1501 shown in FIG. 2 the Gly441 Lys mutant again showed preferential binding to the hTGF-α surface (FIGS. 7A, 7B). Scatchard analysis of the equilibrium binding data (FIGS. 7C, 7D) indicated that whilst binding to the TGF-α surface was similar to that observed with ErbB1501 (KD=77 nM, correlation coefficient R=0.999), the reactivity of the Gly441 Lys mutant towards the EGF surface was now considerably reduced (KD=455 nM, R=0.995). Similar values (78 nM and 469 nM) were obtained by direct non-linear least squares analysis of the binding data using the equation defining steady state equilibrium.

Kinetic analysis of the binding data (Table 2) indicated that the interaction with the immobilised TGF-α could be described by an association rate constant (ka) of $5.2-6.9 \times 10^{-5} M^{-1}s^{-1}$ and a dissociation rate constant (kd) of $0.025 s^{-1}$ giving a KD=kd/ka of 36-44 nM. The corresponding interaction with EGF was described by a ka of $1.9-2.3 \times 10^{-5} M^{-1}s^{-1}$ and a significantly faster kd of $0.103 s^{-1}$ giving a KD=kd/ka of 442-545 nM, in good agreement with the results observed from the thermodynamic analysis.

TABLE 2

| Kinetic analysis of the binding of Gly441Lys sErbB1501 to immobilised hEGF and hTGF-α. | | | |
| --- | --- | --- | --- |
| Interaction | $k_a (M^{-1}s^{-1}) \times 10^{-5}$ | $k_d (s^{-1})$ | $K_D$ (nM) |
| TGF-α | 5.2-6.9 | 0.025 | 36-48 |
| EGF | 1.9-2.3 | 0.103 | 442-545 |

EXAMPLE 6

ErbB1501.Fc Fusion Protein—Ligand Binding Studies

A previous published study had demonstrated that the full-length extracellular domain of ErbB1, expressed as an Fc fusion protein homodimer, bound a number of EGF ligands with IC50 values ranging from 1-10 nM (29), while the corresponding heterodimer with ErbB2 showed at best a two-fold increase in affinity. Using a monolabelled Eu-EGF (Wallac) as trace, we show that the truncated form of the extracellular domain of the EGF receptor, expressed as an Fc fusion homodimer, binds EGF ligand with 10-fold higher affinity than that reported for the full-length ErbB1 ectodomain-Fc fusion protein (30) (see FIG. 8).

EXAMPLE 7

ErbB3500.Fc and ErbB4497.Fc Fusion Proteins—Ligand Binding Studies

ErbB3 and ErbB4 Fc constructs, incorporating the corresponding EGF receptor domains used in ErbB1 501.Fc, were assembled and analysed following transient transfection. In preliminary studies, the full-length erbB4 ectodomain Fc fusion protein, expressed as a homodimer and with ErbB2 ectodomain Fc fusion protein as a heterodimer, was used to validate the data of Fitzpatrick et. al. (30). As demonstrated in FIG. 9, the full-length receptor Fc homodimer exhibits an $IC_{50}$ value for heregulin β(HRGβ) of 18 nM, which is in good agreement with that previously reported (5.1 nM; (29)) allowing for differences in trace ligand preparation. We also find that co-expression of ErbB2 has dramatic affect on the $IC_{50}$ value for ligand, resulting in an increase by two orders of magnitude. Jones et. al. (29) report an increase in $IC_{50}$ of 200-fold using the heterodimer receptors; again, this probably reflects differences in assay format.

The $IC_{50}$ values obtained using the truncated forms of ErbB3 and ErbB4 as homodimer Fc fusion proteins are shown in FIG. 10. While ErbB3 500.Fc has an $IC_{50}$ of 0.49 nM for HRGβ, the value obtained for ErbB4 497.Fc (0.057 nM) approaches that obtained for the full-length ectodomain ErbB2/4 Fc heterodimer reported by Genentech (0.025 nM; (30)).

DISCUSSION

The characteristics of truncated versions of EGFR ectodomains (ErbB1 501, ErbB3 500 and ErbB4 497) that bind hEGF, TGF-α (ErbB1 501) and HRGβ (ErbB3 500 and ErbB4 497) with high affinity are described herein. The KD values of 13-21 nM for hEGF binding to ErbB1501 are similar to those, (15-30 nM), seen with chemically cross-linked dimers of full-length EGFR ectodomain and are 10 to 25-fold higher than the values generally reported for soluble, full-length EGFR ectodomain derived from either A431 tumour cells, transfected Sf9 insect cells or CHO cells.

ErbB1 501, which lacks most of (6 of 7 modules of) CR2, exhibits ligand-induced receptor dimerisation indicating that the regions responsible for dimerisation are unlikely to include CR2. It also confirms that membrane anchoring is not required for the generation of high affinity dimers in contrast to the situation with ErbB2/ErbB3 heterodimers and neuregulin. The ultracentrifugation analyses showed that the binding sites on ErbB1 501 were saturated, and the extent of dimerisation began to plateau, at molar ratios greater than of 1:1 (FIG. 5C), even at the relatively low concentration of ErbB1 501 of 5 µM (320 µg/ml). This compares favourably with the small angle X-ray scattering data and our previous analytical ultracentrifugation analyses that showed that ErbB1 621 dimerisation, induced by EGF or TGF-α binding, reached a maximum when the ratio of EGF/ErbB1 was 1:1.

It is envisaged that the truncated constructs of the present invention will have therapeutic potential given their high affinity for ligand and their ability to competitively inhibit EGF-induced proliferation responses in a model cell system. The inhibition shown by ErbB1 501, for example, was greater than that achieved in the same assay with a neutralising monoclonal antibody raised against the receptor (Mab528), chimeric forms of which (C225) are currently in clinical trials.

ErbB1 501 was also employed to investigate the residue responsible for the differential binding between hTGF-α and hEGF observed with chicken EGFR (9). These data demonstrate that the Lys442 in chicken EGFR, which corresponds to Gly441 in hEGFR, is the residue responsible for discriminating between hTGF-α and hEGF binding.

A number of studies have described the ligand-binding characteristics of isoforms of the ectodomains of different EGF receptor family members, either alone or as Fc fusion proteins. Full-length ectodomain homodimers of ErbB3 and ErbB4, fused to the human IgG1 Fc domain, bind their respective ligands with a range of affinities ($IC_{50}$ values 1-1000 nM;). However, heterodimerisation with the corresponding ErbB2 ectodomain Fc fusion protein is required before very high affinity binding (<1 nM) of the sort observed for cell-surface heterodimers is achieved (30). Our present studies indicate that truncated ectodomain fragments of ErbB1, 3 and 4, expressed as Fc fusion protein homodimers, bind ligand with very high affinity (<1 nM). In the example of ErbB4, the affinity approaches that reported for the heterodimer of the full length ectodomain Fc fusion proteins of ErbB2 and ErbB4 (30).

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the invention.

REFERENCES

1. Burgess AW and Thumwood CM. (1994) Pathology 26, 453-463
2. Bajaj, M., Waterfield, M. D., Schlessinger, J., Taylor, W. R. and Blundell, T. (1987) Biochim.Biophys. Acta. 916, 220-226
3. Ward, C. W., Hoyne, P. A. and Flegg, R. H. (1995) Proteins-Struct. Funct. Genet. 22, 141-153
4. Lax, I., Johnson, A., Howk, R., Sap, J., Bellot, F., Winkler, M., Ullrich, A., Vennstrom, B., Schlessinger, J., and Givol, D. (1988) Molec. Cellul. Biol. 8, 1970-1978
5. Sandgreen, E. P., Luettke, N. C., Palmiter, R. D., Brinster, R. L., Lee, D. C. (1990) Cell 61, 1121-1135
6. Hines, N. E. (1993) Semin. Cancer Biol. 4, 19-26
7. Stanley, P. (1989) Molec. Cellul. Biol. 9, 377-383
8. Saxon, M. L. and Lee, D. C. (1999) J. Biol. Chem. 274, 28356-28362
9. Kohda, D., Odaka, M., Lax, I., Kawasaki, H., Suzuki, K., Ullrich, A., Schlessinger, J. and Inagaki, F. (1993) J. Biol. Chem. 268, 1976-1981
10. Souriau, C., Fort, P., Roux, P., Hartley, O., Lefranc, M-P., Weill, M., 1997, Nucleic Acids Res. 25:1585-1590
11. Rockwell, P., O'Connor, W.J., King, K., Goldstein, N.I., Zhang, L.M., Stein, C.A., 1997, Proc Natl Acad Sci USA 94:6523-6528;
12. Prewett, M., Rothman, M., Waksal, H., Feldman, M., Bander, N.H., Hicklin, D.J., 1998 Clin Cancer Res 4:2957-2966

13. Ullrich, A., Coussens, L., Hayflick, J. S., Dull, T. J., Gray, A., Tam, A. W., Lee, J., Yarden, Y., Libermann, T. A., Schlessinger, J., Downard, J., Mayes, E. L. V., Whittle, N., Waterfield, M. D. and Seeburg, P. H. (1984) Nature 309, 418-425
14. Bebbington, C.R. and Hentschel, C. C. G. (1987) in DNA Cloning (Glover, D., ed.), Vol. III, pp.163-188, IRL Press, Oxford, U.K.
15. McKern, N. M., Lou, M., Frenkel, M. J., Verkuylen, A., Bentley, J. D., Lovrecz, G. O., Ivancic, N., Elleman, T. C., Garrett, T. P. J., Cosgrove L. & Ward, C. W. (1997) Protein Sci. 6, 2663-2666
16. Norrander, J., Kempe, T. and Messing, J. (1983) Gene 26, 101-106
17. Carter, P. (1987) Methods Enzymol. 154, 382-403
18. Sanger, F., Nicklen, S. and Coulson, A. R. (1977) Proc. Natl. Acad. Sci. U.S.A. 74, 5463-5467
19. Gill, G. N., Kawamoto, T., Cochet, C., Le, A., Sato, J. D., Masui, H., McLeod, C., and Mendelsohn, J. (1984) J. Biol. Chem. 259, 7755-7760
20. Nice, E., Lackmann, M., Smyth, F., Fabri, L., Burgess, A. W. (1994) J Chromatogr. A 660, 169-185
21. Catimel B, Domagala T, Nerrie M, Weinstock J, White S, Abud H, Heath J and Nice E, (1999) Prot. Pept. Lett. 6, 319-340
22. Catimel, B., Nerrie, M., Lee, F. T., Scott, A. M., Ritter, G., Welt, S., Old, L. J., Burgess, A. W. and Nice, E. C. (1997) J. Chromatogr. 776, 15-30.
23. Domagala, T., Konstantopoulos, N., Smyth, F., Jorissen, R. N., Fabri, L., Geleick, D., Lax, I., Schlessinger, J., Sawyer, W., Howlett, G. J., Burgess, A. W. and Nice, E. C. (2000) Growth Factors 18, 11-29
24. Morton, T. A. and Myszka, D. G. (1998) Methods Enzymol. 295, 268-294.
25. Hammacher, A., Simpson, R. J. and Nice, E. C. (1996) 271, 5464-5473
26. Minton, A. P. (1994) In Modern Analytical Ultracentrifugation: Acquisition and Interpretation of Data for Biological and Synhtetic Polymer systems. Schuster, T. M. and Laue, T. M. eds, Birkhauser, Boston, p81
27. De Crescenzo, G., Grothe, S., Lortie, R., Debanne, M.T. and O'Connor-McCourt M. (2000) Biochemistry, 9466-9476
28. Nice E. C. and Catimel B. (1999) BioEssays 21, 339-352
29. Jones, J. T. et.al. (1999) FEBS Letters 447:227-231
30. Fitzpatrick, V. D. et.al. (1998) FEBS Letters 431:102-106

We claim:

1. An isolated or purified truncated ErbB4 epidermal growth factor receptor (EGFR) ectodomain comprising at least residues 1 to 488 of ErbB4 (SEQ ID NO:4), the truncated EGFR ectodomain lacking at least the third to seventh modules of the CR2 domain such that a homodimer of the truncated EGFR ectodomain has an increased binding affinity for at least one EGFR ligand when compared to a homodimer of the full length EGFR ectodomain.

2. The truncated EGFR ectodomain as claimed in claim 1 wherein the truncated EGFR ectodomain lacks at least the second to seventh modules of the CR2 domain.

3. The truncated EGFR ectodomain as claimed in claim 1 wherein the truncated EGFR ectodomain further lacks a portion of the first module of the CR2 domain.

4. The truncated EGFR ectodomain as claimed in claim 1 wherein the truncated EGFR ectodomain lacks residues 510-626 of ErbB4 (SEQ ID NO:4).

5. The truncated EGFR ectodomain as claimed in claim 4 wherein the truncated EGFR ectodomain lacks residues 498-626 of ErbB4 (SEQ ID NO:4).

6. The truncated EGFR ectodomain as claimed in claim 1 wherein the truncated EGFR ectodomain comprises residues 1-497 or residues 1-509 of ErbB4 (SEQ ID NO:4).

7. The truncated EGFR ectodomain as claimed in claim 1 wherein the truncated EGFR ectodomain consists of residues 1-497 or residues 1-509 of ErbB4 (SEQ ID NO:4).

8. A chimeric or fusion construct comprising a truncated EGFR ectodomain as claimed in claim 1.

9. The chimeric or fusion construct as claimed in claim 8 wherein the truncated EGFR ectodomain is conjugated to an immunoglobulin constant domain.

10. The chimeric or fusion construct as claimed in claim 9 wherein the construct comprises residues 1-497 of ErbB4 (SEQ ID NO:4) fused to an immunoglobulin constant domain.

11. A homodimer of the chimeric or fusion protein of claim 9.

12. A pharmaceutical composition comprising the truncated EGFR ectodomain as claimed in claim 1 and a pharmaceutically acceptable carrier or diluent.

13. A pharmaceutical composition comprising the chimeric or fusion construct as claimed in claim 9 and a pharmaceutically acceptable carrier or diluent.

* * * * *

SEQUENCE LISTING

```
<160> NUMBER OF SEQ ID NOS: 4

<210> SEQ ID NO 1
<211> LENGTH: 621
<212> TYPE: PRT
<213> ORGANISM: Homo sapiens

<400> SEQUENCE: 1

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190
```

-continued

```
Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser
```

```
              610                 615                 620

<210> SEQ ID NO 2
<211> LENGTH: 631
<212> TYPE: PRT
<213> ORGANISM: Homo sapiens

<400> SEQUENCE: 2

Ser Thr Gln Val Cys Thr Gly Thr Asp Met Lys Leu Arg Leu Pro Ala
1               5                   10                  15

Ser Pro Glu Thr His Leu Asp Met Leu Arg His Leu Tyr Gln Gly Cys
            20                  25                  30

Gln Val Val Gln Gly Asn Leu Glu Leu Thr Tyr Leu Pro Thr Asn Ala
        35                  40                  45

Ser Leu Ser Phe Leu Gln Asp Ile Gln Glu Val Gln Gly Tyr Val Leu
    50                  55                  60

Ile Ala His Asn Gln Val Arg Gln Val Pro Leu Gln Arg Leu Arg Ile
65                  70                  75                  80

Val Arg Gly Thr Gln Leu Phe Glu Asp Asn Tyr Ala Leu Ala Val Leu
                85                  90                  95

Asp Asn Gly Asp Pro Leu Asn Asn Thr Thr Pro Val Thr Gly Ala Ser
            100                 105                 110

Pro Gly Gly Leu Arg Glu Leu Gln Leu Arg Ser Leu Thr Glu Ile Leu
        115                 120                 125

Lys Gly Gly Val Leu Ile Gln Arg Asn Pro Gln Leu Cys Tyr Gln Asp
    130                 135                 140

Thr Ile Leu Trp Lys Asp Ile Phe His Lys Asn Asn Gln Leu Ala Leu
145                 150                 155                 160

Thr Leu Ile Asp Thr Asn Arg Ser Arg Ala Cys His Pro Cys Ser Pro
                165                 170                 175

Met Cys Lys Gly Ser Arg Cys Trp Gly Glu Ser Ser Glu Asp Cys Gln
            180                 185                 190

Ser Leu Thr Arg Thr Val Cys Ala Gly Gly Cys Ala Arg Cys Lys Gly
        195                 200                 205

Pro Leu Pro Thr Asp Cys Cys His Glu Gln Cys Ala Ala Gly Cys Thr
    210                 215                 220

Gly Pro Lys His Ser Asp Cys Leu Ala Cys Leu His Phe Asn His Ser
225                 230                 235                 240

Gly Ile Cys Glu Leu His Cys Pro Ala Leu Val Thr Tyr Asn Thr Asp
                245                 250                 255

Thr Phe Glu Ser Met Pro Asn Pro Glu Gly Arg Tyr Thr Phe Gly Ala
            260                 265                 270

Ser Cys Val Thr Ala Cys Pro Tyr Asn Tyr Leu Ser Thr Asp Val Gly
        275                 280                 285

Ser Cys Thr Leu Val Cys Pro Leu His Asn Gln Glu Val Thr Ala Glu
    290                 295                 300

Asp Gly Thr Gln Arg Cys Glu Lys Cys Ser Lys Pro Cys Ala Arg Val
305                 310                 315                 320

Cys Tyr Gly Leu Gly Met Glu His Leu Arg Glu Val Arg Ala Val Thr
                325                 330                 335

Ser Ala Asn Ile Gln Glu Phe Ala Gly Cys Lys Lys Ile Phe Gly Ser
            340                 345                 350

Leu Ala Phe Leu Pro Glu Ser Phe Asp Gly Asp Pro Ala Ser Asn Thr
        355                 360                 365
```

```
Ala Pro Leu Gln Pro Glu Gln Leu Gln Val Phe Glu Thr Leu Glu Glu
    370                 375                 380

Ile Thr Gly Tyr Leu Tyr Ile Ser Ala Trp Pro Asp Ser Leu Pro Asp
385                 390                 395                 400

Leu Ser Val Phe Gln Asn Leu Gln Val Ile Arg Gly Arg Ile Leu His
                405                 410                 415

Asn Gly Ala Tyr Ser Leu Thr Leu Gln Gly Leu Gly Ile Ser Trp Leu
            420                 425                 430

Gly Leu Arg Ser Leu Arg Glu Leu Gly Ser Gly Leu Ala Leu Ile His
        435                 440                 445

His Asn Thr His Leu Cys Phe Val His Thr Val Pro Trp Asp Gln Leu
    450                 455                 460

Phe Arg Asn Pro His Gln Ala Leu Leu His Thr Ala Asn Arg Pro Glu
465                 470                 475                 480

Asp Glu Cys Val Gly Glu Gly Leu Ala Cys His Gln Leu Cys Ala Arg
                485                 490                 495

Gly His Cys Trp Gly Pro Gly Pro Thr Gln Cys Val Asn Cys Ser Gln
            500                 505                 510

Phe Leu Arg Gly Gln Glu Cys Val Glu Cys Arg Val Leu Gln Gly
        515                 520                 525

Leu Pro Arg Glu Tyr Val Asn Ala Arg His Cys Leu Pro Cys His Pro
    530                 535                 540

Glu Cys Gln Pro Gln Asn Gly Ser Val Thr Cys Phe Gly Pro Glu Ala
545                 550                 555                 560

Asp Gln Cys Val Ala Cys Ala His Tyr Lys Asp Pro Pro Phe Cys Val
                565                 570                 575

Ala Arg Cys Pro Ser Gly Val Lys Pro Asp Leu Ser Tyr Met Pro Ile
            580                 585                 590

Trp Lys Phe Pro Asp Glu Glu Gly Ala Cys Gln Pro Cys Pro Ile Asn
        595                 600                 605

Cys Thr His Ser Cys Val Asp Leu Asp Asp Lys Gly Cys Pro Ala Glu
    610                 615                 620

Gln Arg Ala Ser Pro Leu Thr
625                 630

<210> SEQ ID NO 3
<211> LENGTH: 624
<212> TYPE: PRT
<213> ORGANISM: Homo sapiens

<400> SEQUENCE: 3

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
            20                  25                  30

Leu Tyr Glu Arg Cys Glu Val Val Met Gly Asn Leu Glu Ile Val Leu
        35                  40                  45

Thr Gly His Asn Ala Asp Leu Ser Phe Leu Gln Trp Ile Arg Glu Val
    50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110
```

```
Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
130                 135                 140

Arg Asp Ile Val Arg Asp Ala Glu Ile Val Lys Asp Asn
145                 150                 155                 160

Gly Arg Ser Cys Pro Cys His Glu Val Cys Lys Gly Arg Cys Trp
                165                 170                 175

Gly Pro Gly Ser Glu Asp Cys Gln Thr Leu Thr Lys Thr Ile Cys Ala
                180                 185                 190

Pro Gln Cys Asn Gly His Cys Phe Gly Pro Asn Pro Asn Gln Cys Cys
            195                 200                 205

His Asp Glu Cys Ala Gly Gly Cys Ser Gly Pro Gln Asp Thr Asp Cys
        210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270

His Asn Phe Val Val Asp Gln Thr Ser Cys Val Arg Ala Cys Pro Pro
        275                 280                 285

Asp Lys Met Glu Val Asp Lys Asn Gly Leu Lys Met Cys Glu Pro Cys
    290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                325                 330                 335

Lys Ile Leu Gly Asn Leu Asp Phe Leu Ile Thr Gly Leu Asn Gly Asp
            340                 345                 350

Pro Trp His Lys Ile Pro Ala Leu Asp Pro Glu Lys Leu Asn Val Phe
        355                 360                 365

Arg Thr Val Arg Glu Ile Thr Gly Tyr Leu Asn Ile Gln Ser Trp Pro
    370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
        435                 440                 445

Leu Asn Trp Thr Lys Val Leu Arg Gly Pro Thr Glu Glu Arg Leu Asp
    450                 455                 460

Ile Lys His Asn Arg Pro Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495

Gln Cys Leu Ser Cys Arg Asn Tyr Ser Arg Gly Gly Val Cys Val Thr
            500                 505                 510

His Cys Asn Phe Leu Asn Gly Glu Pro Arg Glu Phe Ala His Glu Ala
        515                 520                 525
```

```
Glu Cys Phe Ser Cys His Pro Glu Cys Gln Pro Met Glu Gly Thr Ala
            530                 535                 540

Thr Cys Asn Gly Ser Gly Ser Asp Thr Cys Ala Gln Cys Ala His Phe
545                 550                 555                 560

Arg Asp Gly Pro His Cys Val Ser Ser Cys Pro His Gly Val Leu Gly
                565                 570                 575

Ala Lys Gly Pro Ile Tyr Lys Tyr Pro Asp Val Gln Asn Glu Cys Arg
            580                 585                 590

Pro Cys His Glu Asn Cys Thr Gln Gly Cys Lys Gly Pro Glu Leu Gln
            595                 600                 605

Asp Cys Leu Gly Gln Thr Leu Val Leu Ile Gly Lys Thr His Leu Thr
            610                 615                 620

<210> SEQ ID NO 4
<211> LENGTH: 626
<212> TYPE: PRT
<213> ORGANISM: Homo sapiens

<400> SEQUENCE: 4

Gln Ser Val Cys Ala Gly Thr Glu Asn Lys Leu Ser Ser Leu Ser Asp
1               5                   10                  15

Leu Glu Gln Gln Tyr Arg Ala Leu Arg Lys Tyr Tyr Glu Asn Cys Glu
            20                  25                  30

Val Val Met Gly Asn Leu Glu Ile Thr Ser Ile Glu His Asn Arg Asp
        35                  40                  45

Leu Ser Phe Leu Arg Ser Val Arg Glu Val Thr Gly Tyr Val Leu Val
    50                  55                  60

Ala Leu Asn Gln Phe Arg Tyr Leu Pro Leu Glu Asn Leu Arg Ile Ile
65              70                  75                  80

Arg Gly Thr Lys Leu Tyr Glu Asp Arg Tyr Ala Leu Ala Ile Phe Leu
            85                  90                  95

Asn Tyr Arg Lys Asp Gly Asn Phe Gly Leu Gln Glu Leu Gly Leu Lys
            100                 105                 110

Asn Leu Thr Glu Ile Leu Asn Gly Gly Val Tyr Val Asp Gln Asn Lys
        115                 120                 125

Phe Leu Cys Tyr Ala Asp Thr Ile His Trp Gln Asp Ile Val Arg Asn
130                 135                 140

Pro Trp Pro Ser Asn Leu Thr Leu Val Ser Thr Asn Gly Ser Ser Gly
145                 150                 155                 160

Cys Gly Arg Cys His Lys Ser Cys Thr Gly Arg Cys Trp Gly Pro Thr
                165                 170                 175

Glu Asn His Cys Gln Thr Leu Thr Arg Thr Val Cys Ala Glu Gln Cys
            180                 185                 190

Asp Gly Arg Cys Tyr Gly Pro Tyr Val Ser Asp Cys Cys His Arg Glu
        195                 200                 205

Cys Ala Gly Gly Cys Ser Gly Pro Lys Asp Thr Asp Cys Phe Ala Cys
    210                 215                 220

Met Asn Phe Asn Asp Ser Gly Ala Cys Val Thr Gln Cys Pro Gln Thr
225                 230                 235                 240

Phe Val Tyr Asn Pro Thr Thr Phe Gln Leu Glu His Asn Phe Asn Ala
                245                 250                 255

Lys Tyr Thr Tyr Gly Ala Phe Cys Val Lys Lys Cys Pro His Asn Phe
            260                 265                 270

Val Val Asp Ser Ser Ser Cys Val Arg Ala Cys Pro Ser Ser Lys Met
        275                 280                 285
```

```
Glu Val Glu Glu Asn Gly Ile Lys Met Cys Lys Pro Cys Thr Asp Ile
    290                 295                 300
Cys Pro Lys Ala Cys Asp Gly Ile Gly Thr Gly Ser Leu Met Ser Ala
305                 310                 315                 320
Gln Thr Val Asp Ser Ser Asn Ile Asp Lys Phe Ile Asn Cys Thr Lys
                325                 330                 335
Ile Asn Gly Asn Leu Ile Phe Leu Val Thr Gly Ile His Gly Asp Pro
            340                 345                 350
Tyr Asn Ala Ile Glu Ala Ile Asp Pro Glu Lys Leu Asn Val Phe Arg
        355                 360                 365
Thr Val Arg Glu Ile Thr Gly Phe Leu Asn Ile Gln Ser Trp Pro Pro
370                 375                 380
Asn Met Thr Asp Phe Ser Val Phe Ser Asn Leu Val Thr Ile Gly Gly
385                 390                 395                 400
Arg Val Leu Tyr Ser Gly Leu Ser Leu Leu Ile Leu Lys Gln Gln Gly
                405                 410                 415
Ile Thr Ser Leu Gln Phe Gln Ser Leu Lys Glu Ile Ser Ala Gly Asn
            420                 425                 430
Ile Tyr Ile Thr Asp Asn Ser Asn Leu Cys Tyr Tyr His Thr Ile Asn
        435                 440                 445
Trp Thr Thr Leu Phe Ser Thr Ile Asn Gln Arg Ile Val Ile Arg Asp
450                 455                 460
Asn Arg Lys Ala Glu Asn Cys Thr Ala Glu Gly Met Val Cys Asn His
465                 470                 475                 480
Leu Cys Ser Ser Asp Gly Cys Trp Gly Pro Gly Pro Asp Gln Cys Leu
                485                 490                 495
Ser Cys Arg Arg Phe Ser Arg Gly Arg Ile Cys Ile Glu Ser Cys Asn
            500                 505                 510
Leu Tyr Asp Gly Glu Phe Arg Glu Phe Glu Asn Gly Ser Ile Cys Val
        515                 520                 525
Glu Cys Asp Pro Gln Cys Glu Lys Met Glu Asp Gly Leu Leu Thr Cys
530                 535                 540
His Gly Pro Gly Pro Asp Asn Cys Thr Lys Cys Ser His Phe Lys Asp
545                 550                 555                 560
Gly Pro Asn Cys Val Glu Lys Cys Pro Asp Gly Leu Gln Gly Ala Asn
                565                 570                 575
Ser Phe Ile Phe Lys Tyr Ala Asp Pro Asp Arg Glu Cys His Pro Cys
            580                 585                 590
His Pro Asn Cys Thr Gln Gly Cys Asn Gly Pro Thr Ser His Asp Cys
        595                 600                 605
Ile Tyr Tyr Pro Trp Thr Gly His Ser Thr Leu Pro Gln His Ala Arg
        610                 615                 620
Thr Pro
625
```